US006239330B1

(12) United States Patent
Duvick et al.

(10) Patent No.: US 6,239,330 B1
(45) Date of Patent: *May 29, 2001

(54) FUMONISIN DETOXIFICATION COMPOSITIONS AND METHODS

(75) Inventors: Jonathan Duvick; Joyce R. Maddox, both of Des Moines; Xun Wang, Johnston, all of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/262,758

(22) Filed: Mar. 4, 1999

Related U.S. Application Data

(60) Division of application No. 08/888,949, filed on Jul. 7, 1997, now Pat. No. 6,025,188, which is a continuation-in-part of application No. 08/484,815, filed on Jun. 7, 1995, now Pat. No. 5,792,931, which is a continuation-in-part of application No. 08/289,595, filed on Aug. 12, 1994, now abandoned.

(51) Int. Cl.[7] ............................ C12N 15/31; C12N 15/55; C12N 15/63; C12N 15/82; A01H 5/00

(52) U.S. Cl. ........................ 800/279; 800/278; 800/295; 800/298; 800/320; 800/320.1; 800/320.2; 800/288; 435/69.1; 435/419; 435/468; 435/196; 536/23.2; 536/23.7; 536/24.1

(58) Field of Search .............................. 435/172.3, 172.1, 435/196, 419, 468, 69.1; 800/208, 200, 279, 278, 295, 298, 320, 320.1, 320.2, 288; 536/23.2, 23.7, 24.1

(56) References Cited

U.S. PATENT DOCUMENTS

| 4,988,586 | 1/1991 | Toyoda et al. | |
|---|---|---|---|
| 5,178,863 | 1/1993 | Toyoda et al. | |
| 5,262,306 | 11/1993 | Robeson et al. | |
| 5,716,820 | * 2/1998 | Duvick et al. | 435/196 |
| 5,792,931 | * 8/1998 | Duvick et al. | 800/205 |

FOREIGN PATENT DOCUMENTS

WO9632007   10/1996  (WO) .

OTHER PUBLICATIONS

Abbas, et al. (1992) Phytotoxicity of Fumonisin $B_1$ on Weed and Crop Species[1,] *Weed Technology*, 6:548–552.
Blackwell, et al. (1994) Production of Carbon 14–Labeled Fumonisin in Liquid Culture, *Journal of AOAC International*, 77(2): 506–511.
Gelderblom, et al. (1993) Structure–Activity Relationships of Fumonisins in Short–Term Carcinogenesis and Cytotoxicity Assays, *Food Chem. Toxic*, 31(6): 407–414.
Van Asch, et al. (1992) Phytotoxicity of Fumonisin $B_1$, Moniliformin, and T–2 Toxin to Corn Callus Cultures, *Phytopathology*, 82(11): 1330–1332.
Vesonder, et al. (1993) Comparison of the Cytotoxicities of Fusarium Metabolites and Alternaria Metabolite AAL–Toxin to Cultured Mammalian Cell Lines, *Arch. Environ. Contam. Toxicol.*, 24: 473–477.
Tanaka, et al. (1993) Structure–Dependent Phytotoxicity of Fumonisins and Related Compounds in a Duckweed Bioassay, *Phytochemistry*, 33(4): 779–785.
He P., et al. (1992) Microbial Transformation of Deoxynivalenol (Vomitoxin), *Applied and Environmental Microbiology*, 58(12): 3857–3863.
Kneusel, et al. (1994) Molecular Characterization and Cloning of an Esterase Which Inactivates the Macrolide Toxin Brefeldin A*, *The Journal of Biological Chemistry*, 269(5): 3449–3456.
Miller, J.D., et al. (1986) Degradation of deoxynivalenol by suspension cultures of the fusarium head blight resistant wheat cultivar Frontana, *Canadian Journal of Plant Pathology*, 8:147–150.
Ueno, et al. (1983) Metabolism of T–2 Toxin in Curtobacterium sp. Strain 114–2, *Applied and Environmental Microbiology*, 46: 120–127.
Utsumi, et al. (1991) Molecular Cloning and Characterization of the Fusaric Acid–resistance Gene from *Pseudomonas cepacia*, *Agric. Biol. Chem.*, 55: 1913–1918.
Vesonder, et al. (1992) Comparative Phytotoxicity of the Fumonisins, AAL–Toxin and Yeast Sphingolipids in *Lemna minor* L. (Duckweed), *Arch Environ. Contam. Toxicol.*, 23: 464–467.
Marth, et al. (1978) Update on molds: degradation of alfatoxin, *J. Food Technol.*, 33: 81–87.
Kneusel, et al. (1990) Detoxification of the macrolide toxin brefeldin A by *bacillus subtilis*, *FEBS Letters*, 275(1–2): 107–110.

(List continued on next page.)

*Primary Examiner*—David T. Fox
*Assistant Examiner*—Medina A. Ibrahim
(74) *Attorney, Agent, or Firm*—Pioneer Hi-Bred International, Inc.

(57) ABSTRACT

Methods for identifying organisms capable of degrading fumonisin. Fumonisin can be incorporated into culture medium for selection of organisms resistant to fumonisin and/or capable of growing on fumonisin as a sole carbon source. Using this method, several organisms have been identified. These organisms can be used to isolate the enzymes and the genes responsible for conferring fumonisin-resistance. The gene can be cloned and inserted into a suitable expression vector so that the protein can be further characterized. Additionally, the DNA encoding for fumonisin degrading enzymes can be used to transform plant cells normally susceptible to Fusarium or other toxin-producing fungus infection. Plants can be regenerated from the transformed plant cells. In this way, a transgenic plant can be produced with the capability of degrading fumonisin, as well as with the capability of producing the degrading enzymes. Methods for detoxification in grain, grain processing, silage, food crops and in animal feed and rumen microbes are also disclosed.

10 Claims, 6 Drawing Sheets

OTHER PUBLICATIONS

Toyoda, et al. (1988) Detoxification of Fusaric Acid by a Fusaric Acid–Resistant Mutant of *Pseudomonas solanacearum* and its Application to Biological Control of Fusarium Wilt of Tomato, *Phytopathology*, 78(10): 1307–1311.

Bunz et al. (1993) Purification of two isosfunctional hydrolases (EC 3.7.1.8) in the degradative pathway for dibenzofuran in Sphingomonas sp. strain RW1, *Biodegradation*, 4:171–178.

Duvick, et al. (1992) Purification and Characterization of a Novel Antimicrobial peptide from Maize (*Zea mays* L.) Kernels*, *The J. of Biol. Chem.*, 267(26):18814–18820.

Kraus et al. (1992) Synthesis of Analogs of Fumonisin B1, *J. of Agri. and Food Chem.*, 40(12): 2331–2332.

Lotti, et al. (1993) Cloning and analysis of *Candida cylindracea* lipase sequences, *Gene*, 124–45–55.

Cygler et al. (1993) Relationship between sequence conservation and three–dimensional structure in a large family of esterases, lipases, and related proteins, *Protein Science*, 2:366–382.

Arpagaus et al. (1991) Use of the Polymerase Chain Reaction for Homology Probing of Butyrylcholinesterase from Several Vertebrates, *The J. of Biol. Chem.*, 266(11): 6966–6974.

Van Asch et al. (1992) Phytotoxicity of Fumonisin B1, Moniliformin, and T–2 Toxin to Corn Callus Cultures, *Phytopathology*, 82: 1330–1332.

Lague et al., Synthesis of Fumonisin Analogs, Abstracts of Papers (Part 2), 204th *American Chemical Society National Metting*, Washington, D.C.USA (Aug. 23–28, 1992).

Zeiss, Hans–Joachim (1991) Enantioselective Synthesis of Both Enantiomers of Phosphinothricin via Asymmetric Hydrogenation of α–Acylamido Acrylates, *J. Org. Chem.*, 56(5): 1783–1788.

* cited by examiner

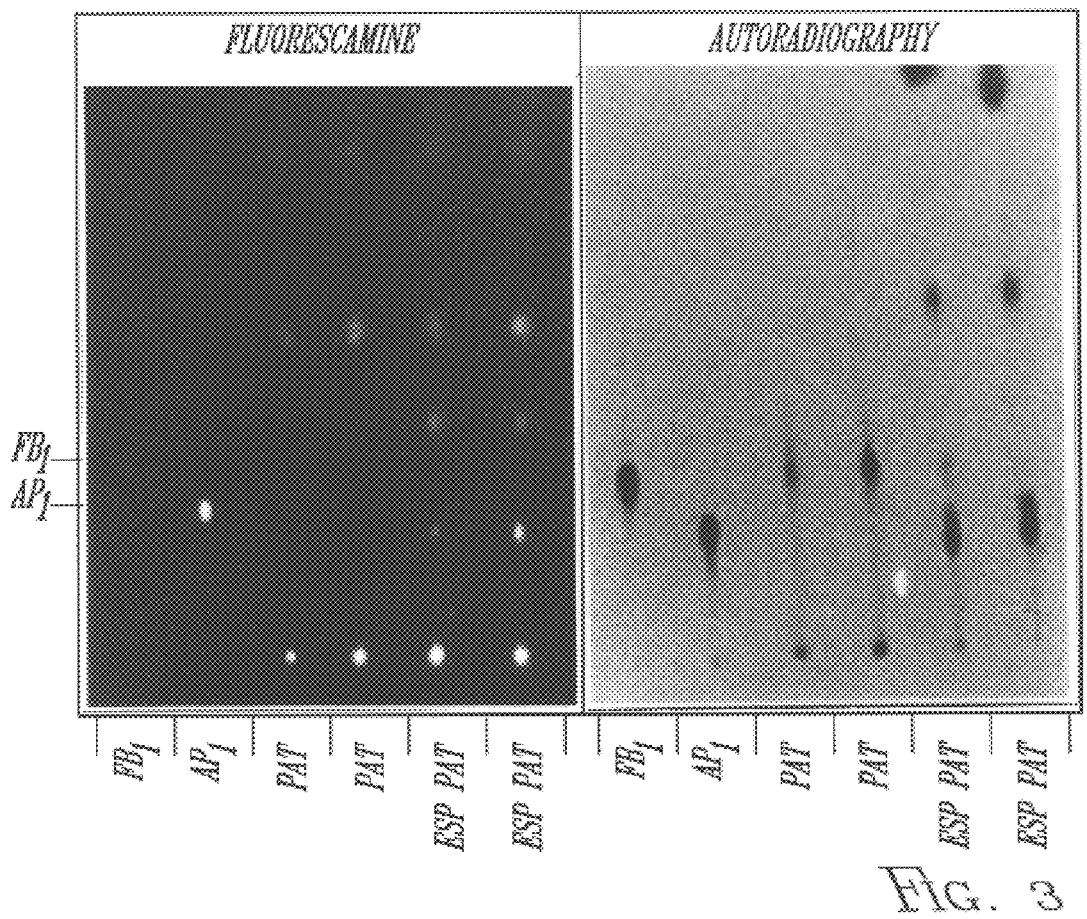

FUMONISIN DETOXIFICATION COMPOSITIONS AND METHODS

CROSS-REFERENCE TO RELATED APPLICATION

This is a divisional of application Ser. No. 08/888,949 filed Jul. 7, 1997, now U.S. Pat. No. 6,025,188 which is a continuation-in-part of application Ser. No. 08/484,815 filed Jun. 7, 1995, now U.S. Pat. No. 5,792,931, which is a continuation-in-part of U.S. application Ser. No. 08/289,595, filed Aug. 12, 1994 now abandoned, and all of which are hereby incorporated by reference.

TECHNICAL FIELD

The present invention relates generally to the detection and isolation of fumonisin resistant organisms and to compositions and methods for the in vivo detoxification or degradation of fumonisin. This method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides and improved agricultural practices. However, as any grower or home gardener can attest, the problems of fungal plant disease continue to cause difficulties in plant cultivation. Thus, there is a continuing need for new methods and materials for solving the problems caused by fungal diseases of plants. These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity. This invention falls into the latter two categories.

Since their discovery and structural elucidation in 1988 (Bezuidenhout S, Gelderblom W, Gorst-Allman C, Horak R, Marasas W, Spiteller B, Vleggaar R (1988) "Structure elucidation of the fumonisins, mycotoxins from *Fusarium moniliforme.*" *Journal Chem Soc, Chem Commun* 1988: 743–745), fumonisins have been recognized as a potentially serious problem in maize-fed livestock. They are linked to several animal toxicoses including leukoencephalomalacia (Marasas W F O, Kellerman T S, Gelderblom W C A, Coetzer J A W, Thiel P (1988) "Leukoencephalomalacia in a horse induced by fumonisin B-1 isolated from *Fusarium moniliforme.*" *Onderstepoort Journal of Veterinary Research* 55: 197–204; Wilson T M, Ledet A E, Owens D L, Rice L G, Nelson H A (1990) "Experimental liver disease in ponies associated with the ingestion of a corn-based ration naturally contaminated with fumonisin $B_1$," *American Association of Veterinary Laboratory Diagnosticians. Abstracts 33rd Annual Meeting*, Denver, Colo., Oct. 7–9, 1990., Madison, Wis., USA) and porcine pulmonary edema (Colvin B M, Harrison L R (1992) "Fumonisin-Induced Pulmonary Edema and Hydrothorax in Swine." *Mycopathologia* 117: 79–82). Fumonisins are also suspected carcinogens. (Geary W (1971) Coord Chem Rev 7: 81; Gelderblom W C A, Kriek N P J, Marasas W F O, Thiel PG (1991) "Toxicity and Carcinogenicity of the Fusarium-Moniliforme Metabolite, Fumonisin-B1, in Rats." *Carcinogenesis* 12: 1247–1251; Gelderblom W C A, Semple E, Marasas W F O, Farber E (1992) "The Cancer-Initiating Potential of the Fumonisin-B Mycotoxins." *Carcinogenesis* 13: 433–437). Fusarium isolates in section Liseola produce fumonisins in culture at levels from 2 to >4000 ppm (Leslie J, Plattner R, Desjardins A, Klittich C (1992) "Fumonisin B1 production by strains from different mating populations of *Gibberella fujikoroi* (Fusarium section Liseola)." *Phytopathology* 82: 341–345). Isolates from maize (predominantly mating population A ) are among the highest producers of fumonisin. (Leslie et al., supra). Fumonisin levels detected in field-grown maize have fluctuated widely depending on location and growing season, but both preharvest and postharvest surveys of field maize have indicated that the potential for high levels of fumonisins exists (Murphy P A, Rice L G, Ross P F (1993) "Fumonisin-B1, Fumonisin-B2, and Fumonisin-B3 content of Iowa, Wisconsin, and Illinois corn and corn screenings." *J Agr Food Chem* 41: 263–266). Surveys of food and feed products have also detected fumonisin (Holcomb M, Thompson H C Jr., Hankins L J (1993) "Analysis of fumonisin B-1 in rodent feed by gradient elution HPLC using precolumn derivation with FMOC and fluorescence detection." *J Agr Food Chem* 41: 764–767; Hopmans E C, Murphy P A (1993) "Detection of Fumonisin-B(1), Fumonisin-B(2), and Funonisin-B(3) and hydrolyzed Fumonisin-B(1) in Corn-Containing foods." *J Agr Food Chem* 41: 1655–1658; Sydenham E W, Shephard G S, Thiel P G, Marasas W F O, Stockenstrom S (1991) "Fumonisin Contamination of Commercial Corn-Based Human Foodstuffs." *J Agr Food Chem* 39: 2014–2018). The etiology of Fusarium ear mold is poorly understood, although physical damage to the ear and certain environmental conditions can contribute to its occurrence (Nelson PE (1992) "Taxonomy and Biology of *Fusarium moniliforme.*" *Mycopathologia* 117: 29–36). Fusarium can be isolated from most field grown maize, even when no visible mold is present. The relationship between seedling infection and stalk and ear diseases caused by Fusarium is not clear. Genetic resistance to visible kernel mold has been identified (Gendloff E, Rossman E, Casale W, Isleib T, Hart P (1986) "Components of resistance to Fusarium ear rot in field corn." *Phytopathology* 76: 684–688; Holley R N, Hamilton P B, Goodman M M (1989) "Evaluation of tropical maize germplasm for resistance to kernel colonization by *Fusarium moniliforme.*" *Plant Dis* 73: 578–580), but the relationship to visible mold to fumonisin production has yet to be elucidated.

Fumonisins have been shown in in vitro mammalian cell studies to inhibit sphingolipid biosynthesis through inhibition of the enzyme sphinganine acyl transferase, resulting in the accumulation of the precursor sphinganine. (Norred W P, Wang E, Yoo H, Riley R T, Merrill AH (1992) "In vitro toxicology of fumonisins and the mechanistic implications." *Mycopathologia* 117: 73–78; Wang E, Norred W, Bacon C, Riley R, Merrill A Jr. (1991) "Inhibition of sphingolipid biosynthesis by fumonisins: implications for diseases associated with *Fusarium moniliforme.*" *J Biol Chem* 266: 14486; Yoo HS, Norred W P, Wang E, Merrill A H, Riley R T (1992) "Fumonisin Inhibition of de Novo Sphingolipid Biosynthesis and Cytotoxicity Are Correlated in LLC-PK1 Cells." *Toxicol Appl Pharmacol* 114: 9–15) It is likely that inhibition of this pathway accounts for at least some of fumonisin's toxicity, and support for this comes from measures of sphinganine:sphingosine ratios in animals fed purified fumonisin (Wang E, Ross P F, Wilson T M, Riley R T, Merrill A H (1992) "Increases in Serum Sphingosine and Sphinganine and Decreases in Complex Sphingolipids in Ponies Given Feed Containing Fumonisins, Mycotoxins Produced by *Fusarium moniliforme.*" *J Nutr* 122: 1706–1716). Fumonisins also affect plant cell growth (Abbas H K, Boyette C D (1992) "Phytotoxicity of fumonisin $B_1$ on weed and crop species." *Weed Technol* 6: 548–552; Vanasch M A J, Rijkenberg F H J, Coutinho T A (1992) "Phytotoxicity of fumonisin $B_1$, moniliformin, and t-2 toxin to corn callus cultures." *Phytopathology* 82: 1330–1332; Vesonder R F, Peterson R E, Labeda D, Abbas H K (1992) "Comparative phytotoxicity of the fumonisins, AAL-Toxin and yeast sphingolipids in Lemna minor L. (Duckweed)." *Arch Environ Contam Toxicol* 23: 464–467). Kuti et al. "Effect of fumonisin B1 aon virulence of Fusarium species isolated from tomato plants." (Abstract, Annual Meeting American Phytopathological Society, Memphis, Tenn.: APS Press 1993) reported on the ability of exogenously added fumonisins to accelerate disease development and increase sporulation of *Fusarium moniliforme* and *F. oxysporum* on tomato.

The toxicity of fumonisins and their potential widespread occurrence in food and feed makes it imperative to find detoxification or elimination strategies to remove the compound from the food chain.

SUMMARY OF THE INVENTION

The present invention provides newly discovered enzymes capable of degrading and detoxifying fumonisins, produced by fermentation of one or more of *Exophiala spinifera*, ATCC 74269, *Rhinocladiella atrovirens*, ATCC 74270, or the bacterium of ATCC 55552. The invention further comprises methods for making enzymes that are capable of detoxifying fumonisins, comprising the step of growing one or more of *Exophiala spinifera*, ATCC 74269, *Rhinocladiella atrovirens*, ATCC 74270, or the bacterium ATCC 55552 in the presence of a fumonisin or the metabolite produced by action of the enzyme on a fumonisin. Alternatively, enzymes are isolated from the seeds or plant parts of a plant transformed and expressing a fumonisin esterase. This invention further provides methods of detoxifying fumonisins, comprising the step of reacting fumonisin with an enzyme derived from *Exophiala spinifera*, ATCC 74269, *Rhinocladiella atrovirens*, ATCC 74270, or the bacterium of ATCC 55552. Fumonisin can be degraded in harvested grain, during the processing of harvested grain, in animal feed, or in plant tissue as, for example, during the use of the plant for silage or as a spray on grain, fruit or vegetables. In addition, the invention provides a method of detoxifying a fumonisin, a structurally related mycotoxin, a fumonisin hydrolysis product, or a hydrolysis product of a structurally related mycotoxin, comprising reacting the said toxin with an AP 1 catabolase.

Genes that code for the fumonisin-degrading enzyme for *Exophiala spinifera*, ATCC 74269 (ESP1) and the bacterium of ATCC 55552 (BEST) have been isolated and sequenced and the amino acid and DNA sequence of the enzymes are provided here. It is known that genes encoding proteins, such as the fumonisin-degrading enzymes, can be identified, isolated, cloned and expressed in transgenic organisms, including several important crop plants. In addition two short amino acid domains of ATLM and TNI are unique to fumonisin esterase and are not found in other known esterase.

This invention also provides a mechanism for selection of transformants: growth of plant cells in the presence of a Fusarium or its mycotoxin favors the survival of plant cells that have been transformed to express the coding sequence that codes for the enzyme of this invention and degrade the toxin. Alternatively, a phytohormone is linked to a tricarballylic acid (TCA) rendering the phytohormone inactive until cleaved by an esterase. When the inactive phytohormone is added to the culture medium only plants expressing an esterase will be able to grow. The esterase can also be used for quantitative evaluation of gene expression using promoter fusions. Substrate containing tricarballylate esters which upon hydrolysis produce a measurable reaction such as but not limited to a color change or fluoresce can be used to measure gene expression. Thus, the coding sequence that codes for the enzyme of this invention can itself be used as a selectable marker, or as a scorable marker by measuring formation of the amino alcohol metabolite or other metabolite.

Another embodiment of the present invention is directed to a DNA construct comprising an expression cassette comprised of:

a) a DNA coding sequence for a polypeptide capable of degrading fumonisin; and b) control sequences that are operably linked to the coding sequence whereby the coding sequence can be transcribed and translated in a host cell, and at least one of the DNA coding sequences or control sequences is heterologous to the host cell.

Preferred embodiments of the subject invention include a host cell stably transformed by a DNA construct as described above; and a method of producing a polypeptide of a recombinant gene comprising:

a) providing a population of these host cells; and b) growing the population of cells under conditions whereby the polypeptide encoded by the coding sequence of the expression cassette is expressed;

c) isolating the resulting polypeptide.

A number of expression systems using the said host cells could be used, such as but not limited to, *E. coli*, yeast or baculovirus. Alternatively, the fumonisin degrading enzymes can be isolated and purified from the seeds or plant parts of a plant expressing the said enzyme.

In yet another embodiment, the present invention is directed to a transgenic plant or plant cells, capable of degrading fumonisin. In another embodiment, the transgenic plant is a maize plant or plant cells capable of degrading fumonisin.

Another embodiment of the subject invention comprises a method of conferring fumonisin degrading abilities to a plant substantially without such abilities comprising transferring to the plant an expressible gene encoding a polypeptide capable of degrading fumonisin.

Additionally, the present invention relates to ruminal microorganisms that have been genetically engineered with the genes imparting fumonisin resistance. These engineered ruminal microorganisms can then be added to feed for consumption by animals susceptible to fumonisin and structurally related mycotoxins.

BRIEF DESCRIPTION OF THE DRAWINGS

FIG. 3 demonstrated fumonisin esterase activity in ESP1-transformed T0 leaf strips imbibed in radiolabeled fumonisin. No such activity was detected in control plants transformed with only the selectable marker PAT (phospninothricin aminotransferase).

DETAILED DESCRIPTION OF THE INVENTION

Figure 1:
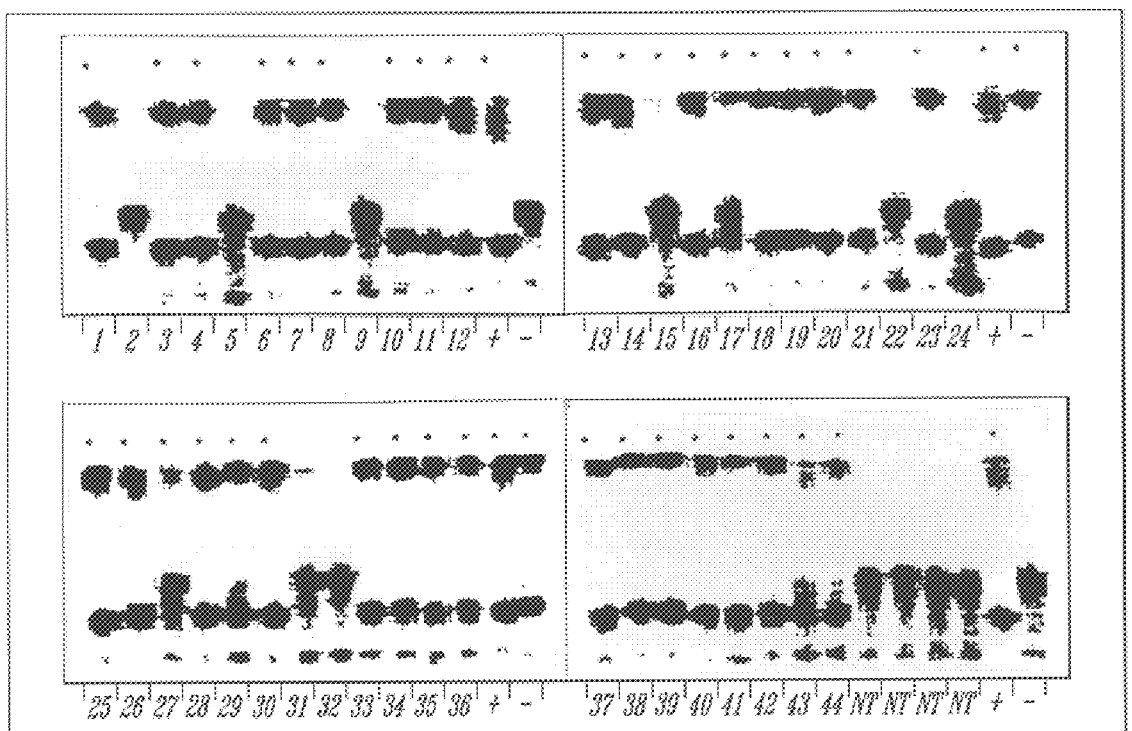
FIG. 1 shows the results of a thin layer chromatographic assay for fumonisin esterase in 44 callus lines bombarded with the esterase gene ESP1 on a maize ubiquitin promoter. The negative controls in the last quadrant show no conversion of 14-C fumonisin to spots of low and high Rf, whereas 41 of 44 transformed lines gave partial or complete conversion to fumonisin hydrolysis products.
Figure 2A:
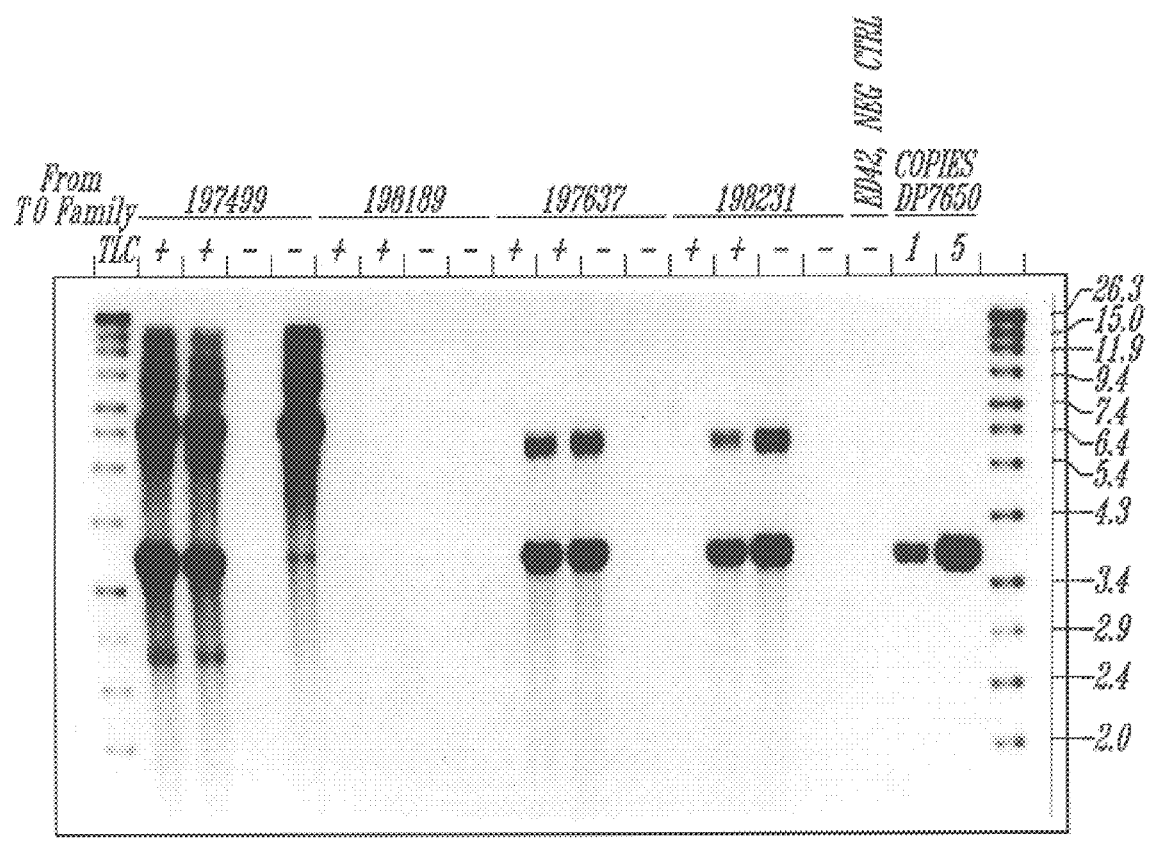
FIGS. 2A and 2B shows DNA gel blots of six T0 families transformed with the fungal esterase gene, either in its native form or fused to the barley alpha amylase leader sequence. Integration patterns ranged from complex (for example 197499, 198271, 203029) to relatively simple (197637, 198231). One family (198189) showed no presence of the transgene.
Figure 2B:
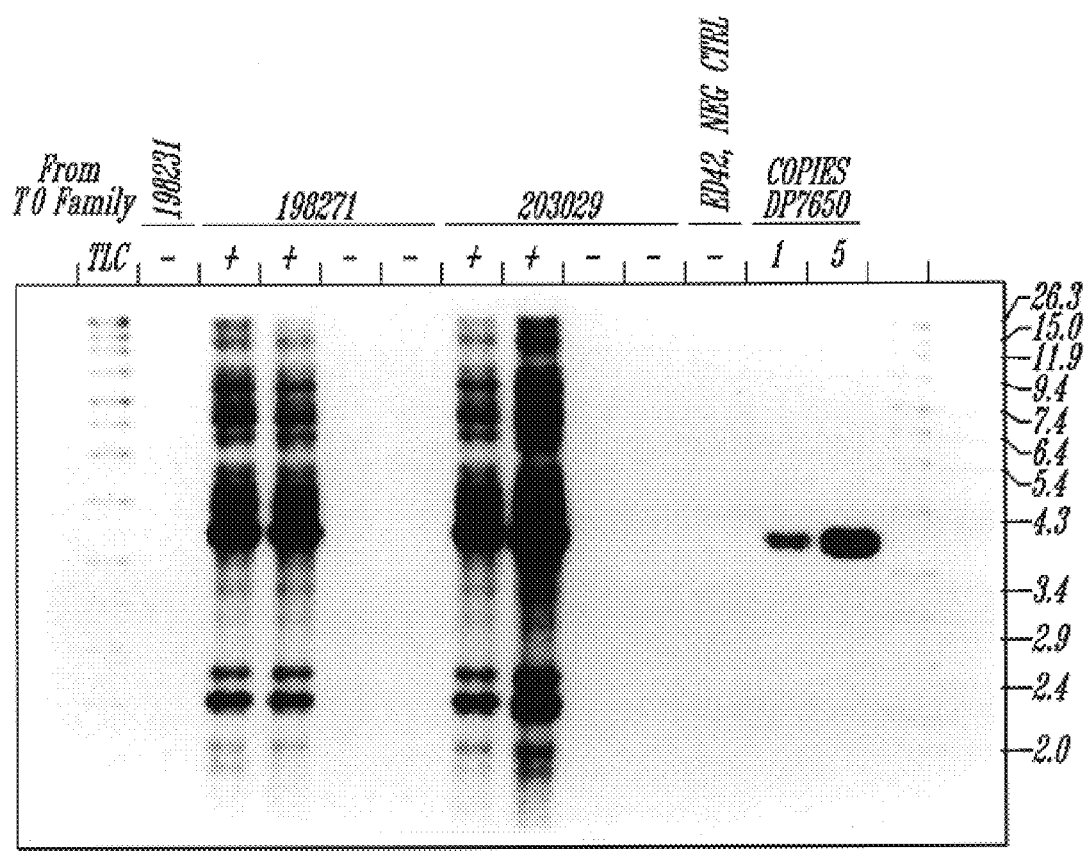

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., J. H. Langenheim and K. V. Thimann, *Botany: Plant Biology and Its Relation to Human Affairs* (1982) John Wiley; *Cell Culture and Somatic Cell Genetics of Plants*, Vol. 1 (I. K. Vasil, ed. 1984); R. V. Stanier, J. L. Ingraham, M. L. Wheelis, and P. R. Painter, *The Microbial World*, (1986) 5th Ed., Prentice-Hall; O. D. Dhringra and J. B. Sinclair, *Basic Plant Pathology Methods*, (1985) CRC Press; Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); and the series *Methods in Enzymology* (S. Colowick and N. Kaplan, eds., Academic Press, Inc.).

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures capable of growth in culture.

A "fumonisin-producing microbe" is any microbe capable of producing the mycotoxin fumonisin or analogs thereof. Such microbes are generally members of the fungal genus Fusarium, as well as recombinantly derived organisms which have been genetically altered to enable them to produce fumonisin or analogues thereof.

By "degrading fumonisin" is meant any modification to the fumonisin molecule which causes a decrease or loss in its toxic activity. Such a change can comprise cleavage of any of the various bonds, oxidation, reduction, the addition or deletion of a chemical moiety, or any other change that affects the activity of the molecule. In a preferred embodiment, the modification includes hydrolysis of the ester linkage in the molecule as a first step. Furthermore, chemically altered fumonisin can be isolated from cultures of microbes that produce an enzyme of this invention, such as by growing the organisms on media containing radioactively-labeled fumonisin, tracing the label, and isolating the degraded toxin for further study. The degraded fumonisin can be compared to the active compound for its phytotoxicity or mammalian toxicity in known sensitive species, such as porcines and equines. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies e.g., using cell suspension cultures.

By "structurally related mycotoxin" is meant any mycotoxin having a chemical structure related to a fumonisin such as fumonisin B 1, for example AAL toxin, fumonisin B2, fumonisin B3, fumonisin B4, fumonisin C1, fumonisin A1 and A2, and their analogs, as well as other mycotoxins having similar chemical structures that would be expected to be detoxified by activity of the fumonisin degradative enzymes elaborated by *Exophiala spinifera*, ATCC 74269, *Rhinocladiella atrovirens*, ATCC 74270, or the bacteria of ATCC 55552.

Two DNA, RNA or polypeptide sequences are "substantially homologous" when at least about 75% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; DNA Cloning, Vols. I & II, supra; Nucleic Acid Hybridization, supra.

Fumonisin Degrading Organisms

The present invention is based on the discovery of organisms with the ability to degrade the mycotoxin fumonisin. In a search for a biological means of detoxifying fumonisins, several dematiaceous hyphomycetes were isolated from field-grown maize kernels. The hyphomycetes were found to be capable of growing on fumonisin B, or $B_2$ (FB1 or $FB_2$) as a sole carbon source, degrading it partially or completely in the process. One species, identified as *Exophiala spinifera*, a "black yeast", was recovered from maize seed from diverse locations in the southeastern and south central U.S. A related species, *Rhinocladiella atrovirens*; was isolated from seed originating in both Iowa and Georgia. A bacterium, given the ATCC number 55552, was isolated and designated isolate 2412.1, from a field-grown maize stalk sample from Johnston, Iowa. This bacterium also showed growth on FB1 as a sole carbon source, and since its taxonomy is not certain a deposit of the strain with the American Type Culture Collection (ATCC) and it is referred to herein by its ATCC deposit number, 55552. Enzyme-active strains of *Exophiala spinifera* (ATCC 74269) and *Rhinocladiella atrovirens* (ATCC 74270) were also deposited. All isolates showed the capability to degrade FB1 in liquid culture. By "degrade" is meant that the enzyme is capable of using fumonisin as a substrate and converting it to a different chemical structure. These studies indicate that the resulting compounds are less toxic than the fumonisins themselves. Overall, only 16 of 70 independent seed samples tested yielded degraders. However, several *E. spinifera* isolates, collected outside the U.S. from non-maize sources, were also found to metabolize fumonisins. Representative isolates of other Exophiala species tested (*E. jeanselmi, E. salmonis, E. piscifera*) did not degrade fumonisins, nor did non-maize Rhinocladiella isolates, including R. atrovirens and R. anceps, nor fungi associated with ear molds including *Fusarium moniliforme, F. graminearum, Aspergillus flavus* and *Diplodia maydis*. Fumonisin-metabolizing black yeasts were found to possess an inducible hydrolase activity that cleaves the tricarbally-late esters of FB1, as monitored by $C_{18}$-thin layer chromatography (TLC) and fluorescence detection of amines. The identity of the resulting amino alcohol compound, designated AP1, was verified by FAB-mass spectroscopy. The latter compound has utility as a chemical indicator of fumonisin metabolism. *E. spinifera* cultures further metabolized AP1 to compounds of unknown identity that were not detectable by amine reagents on TLC. In sealed culture chambers, *E. spinifera* grown on uniformly labeled $^{14}C$ FB, as a sole carbon source, released $^{14}CO_2$ as detected in 1N KOH-saturated filler paper strips, totaling percent of added label in 48 hours. Heat-killed cultures similarly incubated did not release appreciable $^{14}CO_2$. Thus, at least a portion of the fumonisin is fully metabolized by this fungus. Crude, cell-free culture filtrates of the *E. spinifera* isolate designated 2141.10 contained a heat-labile, protease-sensitive hydrolase activity attributed to an enzyme characterized as an esterase with specificity for tricarballylate esters of fumonisins and similar molecules such as AAL-toxin from *Alternaria alternata lycopersici*. This purified esterase is believed to be a new chemical entity, since no commercially available esterases tested were able to hydrolyze the tricarballylate esters of FB1, suggesting a novel enzyme specificity produced by these fungi. Cell-free extracts of *E. spinifera* isolate 2141.10 also contain an AP1 catabolase capable of converting AP1 to a compound lacking a free amine group, possibly a ketone. These enzymes and genes coding for these enzymes, being involved in fumonisin degradation, have utility in detoxification of maize seed pre- or post-harvest. Cell-free lysates of bacterium 2412.1 also contain an AP1 catabolase resulting in a similar compound.

Gene Isolation

Microorganisms demonstrating fumonisin metabolism can be used to create a genomic library using standard techniques, well known in the art. Thus, restriction enzymes can be used to render DNA fragments which can in turn be inserted into any number of suitable cloning vectors. Numerous cloning vectors are known to those of skill in the art, and the selection of an appropriate cloning vector is a matter of choice. The cloning vector need only be capable of transforming a host cell incapable of fumonisin degradation. Examples of recombinant DNA vectors for cloning and host cells which they can transform, shown in parentheses, include the bacteriophage lambda (*E. coli*), pBR322 (*E. coli*), pACYC 177 (*E. coli*), pKT230 (gram-negative bacteria), pGV 1106 (gram-negative bacteria), pLAFRI (gram-negative bacteria), pME290 (non-*E. coli* gram-negative bacteria), pIJ61 (Streptomyces), pUC6 (Streptomyces), YIp5 (Saccharomyces), and YCp19 (Saccharomyces). See, generally DNA Cloning, Vols. I and II, supra, and Maniatis et al., supra. Particularly useful is a cloning vector able to transform *E. coli*.

Once the cloning vector has been inserted into an appropriate host cell, the cells are grown on fumonisin containing media and screened for their ability to degrade fumonisin as previously described. Plasmid DNA inserts from colonies that degrade fumonisin are characterized by subcloning, transposon tagging, and DNA sequence analysis, all well within the skill in the art (see, e.g., Napoli, C., and Staskawicz, B. (1987) *J. Bact.* 169:572–578). Once a coding sequence is determined, recombinant protein molecules able to degrade fumonisin can be produced according to the present invention by constructing an expression cassette and transforming a host cell therewith to provide a cell line or culture capable of expressing the desired protein which is encoded within the expression cassette.

Sequences encoding the fumonisin degradation enzyme can be either prepared directly by synthetic methods based on the determined sequence, or by using the sequence to design oligonucleotide probes to clone the native coding sequence using known techniques. The oligonucleotide probes can be prepared and used to screen a DNA library from an organism able to degrade fumonisin as determined above. The basic strategies for preparing oligonucleotide probes and DNA libraries, as well as their screening by nucleic acid hybridization, are well known to those of ordinary skill in the art. See, e.g., *DNA Cloning, Vol.* 1, supra; *Nucleic Acid Hybridization*, supra; *Oligonucleotide Synthesis*, supra; Maniatis et al., supra.

The coding sequence can be comprised entirely of the coding sequence so derived, or such sequences can be fused to other sequences (e.g., leader sequences) so that a fusion protein is encoded. See, e.g., U.S. Pat. Nos. 4,431,739; 4,425,437 and 4,338,397, the disclosures of which are hereby incorporated by reference. Once an appropriate coding sequence for the fumonisin-degrading enzyme has been prepared or isolated, it can be cloned into any suitable vector or replicon, known in the art. These vectors are described above, with *E. coli* being the host bacterium particularly preferred.

Certain esterases fall into a family that is related by primary sequence and overall structure (Cygler M, Schrag J D, Sussman J L, Harel M, Silman I, Gentry M K, Doctor B P (1993) "Relationship between sequence conservation and 3-Dimensional structure in a large family of esterases, lipases, and related proteins." *Protein Sci* 2: 366–382.). PCR primers were designed based on highly conserved regions of this esterase family and using these primers, a cDNA clone from *Exophiala spinifera* isolate 2141.10 was obtained that showed significant homology to known esterases, and was specifically induced by fumonisin and other inducers. This esterase can be expressed in *E. coli* and its enzyme activity can be measured by means of the TLC assay described above. If no activity is obtained in *E. coli* then expression can be measured in yeast or another eukaryotic system.

Other methods can also be used to clone the gene. Purification of the protein and N-terminal sequencing allow design of specific DNA probes; generation of antibodies from purified protein and screening an expression library; using RNA enrichment methods to obtain cDNAs specific to the induced culture. Once the gene has been confirmed as corresponding to fumonisin esterase, the cDNA clone can easily be ligated into appropriate expression vectors for expression of the enzyme in maize tissue culture cells, transgenic maize, and also in *Fusarium moniliforme* itself, that is useful for studying the mechanisms of pathogenesis associated with the fungus and its toxin. Transformed or transient-expressing maize tissue culture cells can then be evaluated for resistance to fumonisins relative to control transformed tissue, and in fact fumonisin can be used as a selection agent to isolate transformed cells from tissue culture.

Promoters

To complete construction of the expression cassettes, the coding sequence is then operably linked to control sequences such as a promoter, ribosome binding site (for bacterial expression) and, optionally, an operator, so that the DNA sequence encoding the protein is transcribed into messenger RNA in the host cell transformed by the vector containing the expression construction. In order to express a gene, a promoter must be operably linked to that gene. Many different constitutive promoters can be utilized in the instant invention to express a gene. Examples include promoters from plant viruses such as the 35S promoter from cauliflower mosaic virus (CaMV), as described in Odell et al., (1985), *Nature,* 313:810–812, and promoters from genes such as rice actin (McElroy et al., (1990), *Plant Cell,* 163–171); ubiquitin (Christensen et al., (1992), *Plant Mol. Biol.* 12:619–632; and Christensen, et al., (1992), *Plant Mol. Biol.* 18:675–689); pEMU (Last, et al., (1991), *Theor. Appl. Genet.* 81:581–588); MAS (Velten et al., (1984), *EMBO J.* 3:2723–2730); and maize H3 histone (Lepetit et al., (1992), *Mol. Gen. Genet.* 231:276–285; and Atanassvoa et al., (1992), *Plant Journal* 2(3):291–300).

The ALS promoter, a Xba/NcoI fragment 5" to the *Brassica napus* ALS3 structural gene, or a nucleotide sequence having substantial sequence similarity to the XbaI/NcoI fragment, represents a particularly useful constitutive promoter, and is described in published PCT Application WO 96/30530.

In the present invention, an expression vector comprises a constitutive promoter operationally linked to a nucleotide sequence encoding for one of the fumonisin esterase gene. The expression vector and an accompanying, selectable marker gene under the direction of a plant-expressible constitutive promoter are introduced into plant cells, selective agent-resistant cells or tissues are recovered, resistant plants are regenerated and T0 candidates are screened for fumonisin esterase activity in leaf samples.

Additional regulatory elements that may be connected to the fumonisin esterase nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of the fumonisin esterase gene are known, and include, but are not limited to, 3' termination and/or polyadenylation regions such as those of the *Agrobacterium tumefaciens* nopaline synthase (nos) gene (Bevan et al., (1983), *Nucl. Acids Res.* 12:369–385); the potato proteinase inhibitor II (PINII) gene (Keil, et al., (1986), *Nucl. Acids Res.* 14:5641–5650; and An et al., (1989), *Plant Cell* 1:115–122); and the CaMV 19S gene (Mogen et al., (1990), *Plant Cell* 2:1261–1272).

Plant signal sequences, including, but not limited to, signal-peptide encoding DNA/RNA sequences which target proteins to the extracellular matrix of the plant cell (Dratewka-Kos, et al., (1989), *J. Biol. Chem.* 264:4896–4900), the *Nicotiana plumbaginifolia* extension gene (DeLoose, et al., (1991), *Gene* 99:95–100), signal peptides which target proteins to the vacuole like the sweet potato sporamin gene (Matsuka, et al., (1991), *PNAS* 88:834) and the barley lectin gene (Wilkins, et al., (1990), *Plant Cell,* 2:301–313), signal peptides which cause proteins to be secreted such as that of PRIb (Lind, et al., (1992), *Plant Mol. Biol.* 18:47–53), or the barley alpha amylase (BAA) (Rahmatullah, et al. "Nucleotide and predicted amino acid sequences of two different genes for high-pI alpha-amylases from barley." *Plant Mol. Biol.* 12:119 (1989) and hereby incorporated by reference), or from the present invention the signal peptide from the ESP1 or BEST1 gene, or signal peptides which target proteins to the plastids such as that of rapeseed enoyl-Acp reductase (Verwaert, et al., (1994), *Plant Mol. Biol.* 26:189–202) are useful in the invention. The barley alpha amylase signal sequence fused to the mature protein of the ESP1 or BEST1 gene is the preferred construct for the present invention. SEQ ID NO:16 (BAA-ESP1) and SEQ ID NO:17 (BAA-BEST1) are the preferred amino acid sequences from which gene constructs can be made in an expression vector in the present invention.

The construct can then be inserted into an appropriate expression vector. A number of prokaryotic and eukaryotic expression vectors are known in the art. Preferred vectors are prokaryotic expression vectors. A particularly preferred host for such vectors is *E. coli.* The fumonisin-degrading enzyme is then produced by growing the host cells transformed by the expression cassette under conditions which cause the expression of the biologically active protein, as indicated by the host cells ability to degrade fumonisin in the medium on which it is grown, as described above. The protein can be isolated from the host cells and purified for further study. If the protein is not secreted, it may be necessary to disrupt the host cells and purify the protein from the cellular lysate. Various purification techniques, such as HPLC, size-exclusion chromatography, electrophoresis, and immunoaffinity chromatography, are known, and the selection of the appropriate purification and recovery method is within the skill of the art.

Gene Transformation Methods

Numerous methods for introducing foreign genes into plants are known and can be used to insert a fumonisin esterase gene into a plant host, including biological and physical plant transformation protocols. See, for example, Miki et al., (1993), "Procedure for Introducing Foreign DNA into Plants", In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as *Agrobacterium* (Horsch, et al., (1985), *Science* 227:1229–31), electroporation, micro-injection, and biolistic bombardment.

Expression cassettes and vectors and in vitro culture methods for plant cell or tissue transformation and regeneration of plants are known and available. See, for example, Gruber, et al., (1993), "Vectors for Plant Transformation" In: *Methods in Plant Molecular Biology and Biotechnology*, Glick and Thompson, eds. CRC Press, Inc., Boca Raton, pages 89–119.

Agrobacterium-mediated Transformation

The most widely utilized method for introducing an expression vector into plants is based on the natural transformation system of Agrobacteriurn. *A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, (1991), *Crit. Rev. Plant Sci.* 10:1. Descriptions of the Agrobacterium vector systems and methods for Agrohacterizi-n-mediated gene transfer are provided in Gruber et al., supra; Miki, et al., supra; and Moloney et al., (1989), *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey, P. N., and Chua, N. H. (1989) *Science* 244: 174–181. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. application Ser. No. 913,914, filed Oct. 1, 1986, as referenced in U.S. Pat. No. 5,262,306, issued Nov. 16, 1993 to Robeson, et al.; and Simpson, R. B., et al. (1986) *Plant Mol Biol.* 6: 403–415 (also referenced in the '306 patent); all incorporated by reference in their entirety.

Once constructed, these plasmids can be placed into *A. rhizogenes* or *A. tumefaciens* and these vectors used to transform cells of plant species which are ordinarily susceptible to Fusarium or Alternaria infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledons, some gymnosperms, and a few monocotyledons (e.g. certain members of the Liliales and Arales) are susceptible to infection with *A. tumefaciens*. *A. rhizogenes* also has a wide host range, embracing most dicots and some gymnosperms, which includes members of the Leguminosae, Compositae and Chenopodiaceae. Alternative techniques which have proven to be effective in genetically transforming plants include particle bombardment and electroporation. See e.g. Rhodes, C. A., et al. (1988) *Science* 240: 204–207; Shigekawa, K. and Dower, W. J. (1988) *BioTechniques* 6: 742–751; Sanford, J. C., et al. (1987) *Particulate Science & Technology* 5:27–37; and McCabe, D. E. (1988) *BioTechnology* 6:923–926.

Once transformed, these cells can be used to regenerate transgenic plants, capable of degrading fumonisin. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors and cultured under conditions which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, E. A. (1985) *Theor. Appl. Genet.* 69:235–240; U.S. Pat. No. 4,658,082; Simpson, R. B., et al. (1986) *Plant Mol. Biol.* 6: 403–415; and U.S. patent applications Ser. Nos. 913,913 and 913,914, both filed Oct. 1, 1986, as referenced in U.S. Patent 5,262,306, issued Nov. 16, 1993 to Robeson, et al.; the entire disclosures therein incorporated herein by reference.

Direct Gene Transfer

Despite the fact that the host range for Agrobacterium-mediated transformation is broad, some major cereal crop species and gymnosperms have generally been recalcitrant to this mode of gene transfer, even though some success has recently been achieved in rice (Hiei et al., (1994), *The Plant Journal* 6:271–282). Several methods of plant transformation, collectively referred to as direct gene transfer, have been developed as an alternative to Agrobacterium-mediated transformation.

A generally applicable method of plant transformation is microprojectile-mediated transformation, where DNA is carried on the surface of microprojectiles measuring about 1 to 4 $\mu$m. The expression vector is introduced into plant tissues with a biolistic device that accelerates the microprojectiles to speeds of 300 to 600 m/s which is sufficient to penetrate the plant cell walls and membranes. (Sanford et al., (1987), *Part. Sci. Technol.* 5:27; Sanford, 1988, *Trends Biotech* 6:299; Sanford, (1990), *Physiol. Plant* 79:206; Klein et al., (1992), *Biotechnology* 10:268).

Another method for physical delivery of DNA to plants is sonication of target cells as described in Zang et al., (1991), *Bio/Technology* 9:996. Alternatively, liposome or spheroplast fusions have been used to introduce expression vectors into plants. See, for example, Deshayes et al., (1985), *EMBO J.* 4:2731; and Christou et al., (1987), *PNAS USA* 84:3962. Direct uptake of DNA into protoplasts using $CaCl_2$ precipitation, polyvinyl alcohol or poly-L-ornithine have also been reported. See, for example, Hain et al., (1985), *Mol. Gen. Genet.* 199:161; and Draper et al., (1982), *Plant Cell Physiol.* 23 :451. Electroporation of protoplasts and whole cells and tissues has also been described. See, for example, Donn et al., (1990), In: *Abstracts of the VIIth Int'l. Congress on Plant Cell and Tissue Culture IAPTC*, A2–38, page 53; D'Halluin et al., (1992), *Plant Cell* 4:1495–1505; and Spencer et al., (1994), *Plant Mol. Biol.* 24:51–61.

Thus, DNA encoding a protein able to inactivate fumonisin can be isolated and cloned in an appropriate vector and inserted into an organism normally sensitive to the Fusarium or its toxin. Organisms expressing the gene can be easily identified by their ability to degrade fumonisin. The protein capable of degrading fumonisin can be isolated and characterized using techniques well known in the art. Furthermore, the gene imparting fumonisin-resistance can be transferred into a suitable plasmid, and transformed into a plant. Thus, a fumonisin-degrading transgenic plants can be produced.

Isolation of Fumonisin Degrading Enzymes

Fumonisin degrading enzymes can be obtained from a variety of sources. *Exophiala spinefera*, ATCC 74269, *Rhinocladiella atrovirens*, ATCC 74270, or the bacterium of ATCC 55552, can be induced to produce fumonisin degrading enzymes by cultivating the organism on an agar culture containing fumonisin or one of its metabolic breakdown products. Once the culture has been induced to express a fumonisin degrading enzyme, the enzyme can then be isolated and purified by a variety of methods know tho those skilled in the art. See for example, Heney and Orr, 1981, *Anal Biochem.* 114:92–96 and herein incorporated by reference.

Alternatively, one of the genes for fumonisin degrading enzymes described in the present invention can be placed in the appropriate expression vector and then introduced into a microorganism, such as but not limited to, *E. coli*, yeast or baculovirus. Such expression systems are well known in the art. (See for example, Clark, M. *Plant Molecular Biology: A Laboratory Manual*, (1997), Springer-Verlag).

In addition, one of the genes for fumonisin esterase or the AP1 catabolase placed in the appropriate plant expression vector can be used to transform plant cells. The enzyme can then be isolated from plant callus or the transformed cells can be used to regenerate transgenic plants. Such transgenic plants can be harvested, and the appropriate tissues (seed or leaves, for example) can be subjected to large scale protein extraction and purification techniques, and the fumonisin degradation enzymes or AP1 catabolases can be isolated for use in fumonisin and fumonisin hydrolysis product detoxification processes.

Use of enzyme combinations to effect complete detoxification/degradation of fumonisins.

AP1, the product of fumonisin esterase activity on FB1, remains substantially unmodified in maize tissues we have tested. In the preferred embodiment of this invention, the esterase gene from either *Exophiala spinifera* 2141.10 or bacterium 2412.1 is combined with the AP1 catabolase from one or the other of these organisms, such that both enzymes are secreted to the cell wall (apoplast) in the same tissues and together result in complete loss of toxicity of fumonisin. Specifically, the esterase enzyme hydrolytically removes the tricarballylate esters from the backbone, which allows the AP1 catabolase to deaminate the AP1 molecule, rendering it nontoxic to the plant or consumers of the plant tissue. Furthermore, *Exophiala spinifera* 2141.10 and bacterium 2412.1 can metabolize FB1 or AP1 to $CO_2$, indicating that further catabolic enzymes are present that act on the carbon skeleton of AP1 and could readily be cloned and used to effect further breakdown of the deaminated AP1. Likewise, a partial or complete fumonisin catabolic pathway can be expressed coordinately in a recombinant microorganism to detoxify fumonisins or their analogs in environments other than the maize plant.

Use of Fumonisin Esterase as a Screenable Marker Enzyme or Alternatively as a Selectable Marker Cloned microbial esterases (ESP1 and BEST1) hydrolyze the tricarballylate side chains of fumonisins. These esterases are substrate-specific, in that they can hydrolyze tricarballylate esters of several toxins including fumonisins $B_1$ and $B_2$, AAL-toxin, and some synthetic fumonisin analogs, but do not hydrolyze other common esters such as naphthyl acetate ester or fatty acyl esters. Conversely, commercially available esterases and lipases do not hydrolyze the TCA esters of fumonisins, suggesting that this moiety is difficult to hydrolyze due to steric or charge interference. TCA, although similar to citrate, is an uncommon metabolite in nature in either free or esterified form. Therefore the term "fumonisin esterase" is used in a generic sense to denote microbial enzymes that can hydrolyze the TCA ester.

Fumonisin esterases also hydrolyze synthetic tricarballylate esters of other molecules including such commonly used chromogenic or fluorigenic substrates such as umbelliferone or alpha naphthol. Other esterase enzymes, such as those commonly found in cell extracts, would be unlikely to hydrolyze TCA esters, based on the observation of no "background" hydrolysis of fumonisin in plant extracts. These properties of high specificity and low background would make the fumonisin esterases potentially useful for transgene research as marker enzymes (as scorable markers similar to B-glucuronidase or GUS) or for hydrolysis of "cryptic" hormones or toxins for selection schemes (selectable markers). Although this invention is particularly useful for plant systems, this invention could also be used in other types of systems including but not limited to, insect, mammalian and microbial systems.

The fumonisin esterase Esp1 has been expressed and shown to be active in transgenic maize and leads to a high proportion of extracellular enzyme. This could be a useful property when an extracellular marker enzyme is needed. B-glucuronidase (GUS) is a commonly used marker enzyme in transgenic work, but it is difficult to engineer secreted forms of the enzyme. Secretion is a desirable feature when trying to design nondestructive assay systems where the substrate contacts the enzyme without requiring passage of the cell membrane barrier. Esterase is readily secreted in active form, so it does not have this drawback. Also, plant cells contain some "background" B-glucuronidase activity, which can usually be avoided by manipulating assay pH. However this may be undesirable especially in a nondestructive assay where pH cannot be manipulated. The inventors have not detected any background hydrolysis of fumonisin esters by maize enzymes; only when the fumonisin esterase is added is hydrolysis seen. Thus, this system would alleviate the background problems of GUS. This may be particularly important where a "nonleaky" system is needed with a hormone precursor-based selection scheme, for example. Another advantage of using a fumonisin esterase based maker enzyme system is that it represents a second possible marker system to use in combination with the GUS system, in situations where two independent markers are needed.

The fumonisin esterase could also be used to cleave a protoxin or proherbicide compound to an active form that would kill cells expressing active esterase. This would be useful in causing ablation of certain cell types or tissues using a tissue-sepcific promoter driving the esterase. Cell death would result from exogenous application of the protoxin, which would be inert to all cells not expressing the esterase. Applications include genetically engineered sterility in a crop such as maize where gametes must be rendered inviable for hybrid production; and developmental studies in which certain cell types are purposely ablated to study the effect on subsequent development. The negligible background esterase activity in plant tissue is again and advantage, since any leakiness can cause unwanted cell death.

Alternatively, this invention could be used as a method for selection of transformants, in other words as a selectable marker. A fumonisin esterase gene operably linked to a promoter and then transformed into a plant cell by any of the methods described above would express the degradative enzyme. When the plant cells are placed in the presence of either a fumonisin or a phytotoxic analog in culture only the transformed cells would be able to grow. Thus, growth of plant cells in the presence of a mycotoxin favors the survival of plant cells that have been transformed to express the coding sequence that codes for one of the enzymes of this invention and degrades the toxin. When the fumonisin esterase cassette is co-transformed with another gene of interest and then placed in the presence of a fumonisin or a phytotoxic analog, this invention would allow for selection of only those plant cells that contain the gene of interest. In the past antibiotic resistance genes have been used as selectable markers. Given the current concerns by consumers and environmentalist over use of antibiotic genes and the possibility of resistant microorganisms arising due to this use, a non-antibiotic resistant selectable marker system such as the present invention, fulfills this very important need.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE 1

Chemicals and reagents.

All chemicals were reagent grade or better unless otherwise indicated. Fumonisin $B_1$ and $B_2$ were obtained from Sigma Chemical Co. Partially purified fumonisins (eluate from C8 column) were obtained from Dr. Pat Murphy (Iowa State University). AAL-toxin (TA isomer) was a gift of Dr. David Gilchrist (University of California-Davis).

Plant tissue samples.

Mature, field-grown maize seed was obtained from maize breeding locations of Pioneer Hi-Bred International, Inc. in the Southeast, Midwest and South Central regions of the U.S. Seed was stored at room temperature in individual packets.

Fungal and bacterial isolates.

Exophiala and Rhinocladiella isolates from maize were isolated as described below. Other isolates were obtained from Dr. C. J. Wang (Syracuse, N.Y.), Dr. Michael McGinnis (Case Western Reserve University, Cleveland, Ohio), and from the American Type Culture Collection (Bethesda, Md.). *Fusarium graminearum* [*Gibberella zeae* (Schw.) Petsch], *Diplodia majdis*, and *Fusarium moniliforme* Sheld., were obtained from the microbial culture collection of Pioneer Hi-Bred International, Inc. *Aspergillus flavus* (Schw.) Petsch, isolate CP22, was obtained from Don Sumner at the University of Georgia (Tifton, Ga.). Bacterium, ATCC 55552, was isolated from maize stalk tissue as described below.

Isolation methods.

Individual kernels, either intact or split in two with a sterile razor blade, were rinsed for 1 hr in 5 ml sterile water with agitation. From 1 to 5 $\mu$l of the rinse fluid was added to 100 $\mu$L of sterile, carbon-free mineral salts medium +FB1 (MS-FB1) (1 g/liter $NH_3SO_4$, 1 g/liter $K_2HPO_4$, 1 g/liter NaCl, 0.2 g/liter $MgSO_4.7H_2O$, pH 7.0) containing FB1 (Sigma Chemical Co.) at 0.5 to 1.0 mg/ml). The pH of the medium was approx. 6.0 after addition of FB1. After 1 to 2 weeks incubation at 28° C. in the dark, serial 10-fold dilutions were made in sterile $dH_2O$, and aliquots were plated onto 1.2% Bacto-agar containing 0.1% yeast extract, 1% Bacto-peptone and 0.1% dextrose (YPD agar). Fungal and bacterial colonies that appeared on agar were transferred onto fresh plates and individual colonies were evaluated for fumonisin metabolizing ability by inoculating them into fresh MS-FB1. Loss of fumonisin from the medium was monitored periodically by spotting 0.5 to 1 microliter aliquots of culture supernatant on $C_{18}$ silica gel plates that were then air-dried and developed as described below (see Analysis of fumonisins and metabolism products).

Direct isolation of black yeasts from seed was accomplished by plating 100 microliters of seed wash fluid onto YPD or Sabouraud agar augmented with cycloheximide (500 mg/liter) and chloramphenicol (50 mg/liter). Plates were incubated at room temperature for 7–14 days, and individual pigmented colonies that arose were counted and cultured for analysis of fumonisin-degrading ability as described above.

For stalk isolations, mature stalk samples 0.5×0.5×2 cm were taken from Southern-type maize inbreds grown in Johnston, Iowa by Pioneer Hi-Bred International, Inc., a seed company, in 1993. One-inch sections of the center (pith) or the outside of non-surface-sterilized stalk were cut and placed in 10 ml. sterile water in a small, sterilized tube. The tubes were shaken for 1 hour, and then 2 $\mu$l of washate were withdrawn and used to inoculate 100 $\mu$l of MS-FB1 in a microtiter plate. Subsequent steps were as above.

Analysis of fumonisins and metabolism products.

Analytical thin-layer chromatography was carried out on 100% silanized $C_{18}$ silica plates (Sigma #T-7020; 10× 10 cm; 0.1 mm thick) by a modification of the published method of Rottinghaus (Rottinghaus, G. E., Coatney, C. E., and Minor, H. C., A rapid, sensitive thin layer chromatography procedure for the detection of fumonisin b-1 and b-2, *J Vet Diagn Invest*, 4, 326 (1992), and herein incorporated by reference).

Sample lanes were pre-wet with methanol to facilitate sample application. After application of from 0.1 to 2 $\mu$l of aqueous sample, the plates were air-dried and developed in MeOH:4% KCl (3:2) or MeOH:0.2 M KOH (3:2) and then sprayed successively with 0.1 M sodium borate (pH 9.5) and fluorescamine (0.4 mg/ml in acetonitrile). Plates were air-dried and viewed under long wave UV.

Alkaline hydrolysis of FB1 to AP1.

FB1 or crude fumonisin $C_8$ material was suspended in water at 10–100 mg/ml and added to an equal volume of 4 N NaOH in a screw-cap tube. The tube was sealed and incubated at 60° C. for 1 hr. The hydrolysate was cooled to RT and mixed with an equal volume of ethyl acetate, centrifuged at 1000 RCF for 5 minute and the organic (upper) layer recovered. The pooled ethyl acetate layers from two successive extractions were dried under $N_2$ and resuspended in $dH_2O$. The resulting material (the aminopentol of FB1 or "AP1") was analyzed by TLC.

Tables 1 and 2 illustrate the results of efforts to isolate a fumonisin-degrading enzyme from a wide assortment of sources. As is noted, *E. spinifera* isolates from maize seed from various locations were always able to produce a fumonisin-degrading enzyme when grown on fumonisin as a sole carbon source (Table 1), as were *E. spinifera* isolates from other sources from around the world (Table 2). Some samples of *Rhinocladiella atrovirens* from maize seed were also able to produce this enzyme (Table 1). Other species of Exophiala and other sources and species of Rhinocladiella were routinely unable to produce the enzyme, even when isolated from plant-related sources (Table 2).

TABLE 1

Dematiaceous fungi isolated from maize seed that degrade fumonisin

| Isolate # | Species | Location of origin | Isolated from | Appearance[1] | Modification of substrates | |
|---|---|---|---|---|---|---|
| | | | | | FB1 | AP1 |
| 2369.E7 | Exophiala spinifera | Tifton, GA | Maize seed (3293) | clean | + | + |
| 2369.G5 | Exophiala spinifera | Tifton, GA | Maize seed (3379) | clean | + | + |
| 2174.A4 | Exophiala spinifera | Tifton, GA | Maize seed (inbred) | moldy | + | + |
| 2369.F7 | Exophiala spinifera | Winterville, NC | Maize seed (3170) | moldy | + | + |
| 2369.H9 | Exophiala spinifera | Winterville, NC | Maize seed (3379) | moldy | + | + |
| 2141.10 | Exophiala spinifera | Winterville, NC | Maize seed (unk) | moldy | + | + |
| 2174.C6 | Rhinocladiella atrovirens | Winterville, NC | Maize seed (unk) | moldy | + | + |
| 2170.2 | Exophiala spinifera | Winterville, NC | Maize seed (inbred) | moldy | + | + |
| 2174.A4 | Exophiala spinifera | Union City, TN | Maize seed (inbred) | moldy? | + | + |
| 2219.H5 | Exophiala spinifera | Union City, TN | Maize seed (inbred) | moldy | + | + |

TABLE 2-continued

Other fungal isolates tested for degradation of fumonisin B1 in liquid culture

| Isolate | Species | Source | Location of Origin | Isolated from | Modification of substrates FB1 | AP1 |
|---|---|---|---|---|---|---|
| 26438 | Exophiala pisciphila | ATCC | Australia | Wheat rhizosphere | – | nt |
| 26272 | Exophiala jeanselmi | ATCC | Canada | Activated sludge | – | nt |
| P-154 | Rhinocladiella atrovirens | C. J. Wang | Chester, NJ | Southern pine pole | – | nt |
| P-330 | Rhinocladiella atrobirens | C. J. Want | Binghamton, NY | Southern pine pole | – | nt |
| P-646 | Rhinocladiella atrovirens | C. J. Wang | Virginia | Southern pine pole | – | nt |
| P-1492 | Rhinocladiella atrovirens | C. J. Wang | Chester, NJ | Southern pine pole | – | nt |
| ED-43 | Rhinocladiella atrovirens | C. J. Wang | Unknown | Douglas-fir pole | – | nt |
| ED-124 | Rhnocladiella atrovirens | C. J. Wang | Unknown | Douglas-fir pole | – | nt |
| 28220 | Rhinocladiella anceps | ATCC | Maryland | Grass | – | nt |
| | | | -Ear mold fungi- | | | |
| FMO001 | Fusarium monoliforme | PH1 | Unknown | Maize | – | nt |
| FGR001 | Fusarium graminearum | PH1 | Unknown | Maize | – | nt |
| CP22 | Aspergillus flavus | PH1 | Unknown | Maize | – | nt |
| DMA001 | Diplodia maydis | PH1 | Unknow | Maize | – | nt |

*Tested both with FB1 and as a sole carbon source and with FB1 amended with 1% sucrose. PH1 = Pioneer Hi-Bred Intl, Inc.

TABLE 3

Frequency of isolation of fumonisin-degrading black yeast isolates from maize seed

| Location of origin | # samples tested | # samples positive | % containing FB1-degrading black yeast | Species identified |
|---|---|---|---|---|
| Weslaco, TX | 8 | 6 | 75.0 | Exophiala spinifera |
| Winterville, NC | 19 | 4 | 47.5 | Exophiala spinifera, Rhinocladiella atrovirens |
| Tifton, GA | 8 | 3 | 37.5 | Exophiala spinifera |
| Union City, TN | 7 | 2 | 28.2 | Exophiala spinifera |
| Johnston, IA | 7 | 1 | 14.3 | Rhinocladiella atrovirens |
| Shelbyville, IL | 3 | 0 | 0 | none |
| Macomb, IL | 4 | 0 | 0 | — |
| Champaign, IL | 3 | 0 | 0 | — |
| Yale, IN | 3 | 0 | 0 | — |
| California | 8 | 0 | 0 | — |
| Total | 70 | 16 | 22.8 | |

Organisms can be screened for their ability to degrade fumonisin using the present methods. In this way, plant, soil, marine and fresh water samples can be screened and organisms isolated therefrom that are able to degrade fumonisin. Alternatively, already isolated microbial strains that are suspected of possessing this capability can be screened. Putative fumonisin-resistant bacteria include bacteria associated with plant species susceptible to Fusarium infection. For instance, bacteria associated with Fusarium-infected tomato and pepper as well as other susceptible plant species, might be expected to degrade fumonisin. Furthermore, members of bacterial genera known to be versatile in their catabolism of complex organic molecules, such as members of the genus Pseudomonas, might degrade fumonisin.

Generally, media used to culture the above microbes will contain a known amount of fumonisin, i.e. from 0.1 to 3 mg of fumonisin per ml of media, more usually from 0.25 to 2 mg per ml of media, and preferably from 0.5 to 1 mg of fumonisin per ml of media.

A further study was performed to determine if colony morphology could be used to determine which strains of these species would produce a fumonisin-degrading enzyme.

The results as shown in Table 4 indicated that *E. spinifera* and *R. atrovirens* colonies having different morphologies could nevertheless produce the fumonisin-degrading enzyme.

TABLE 4

Black yeasts recovered from a single kernel by direct plating seed washates onto YPD + cycloheximide + chloramphenicol[1]

| Isolate | Colony Type on YPD agar | Species | # colonies | # FB1 degr |
|---|---|---|---|---|
| 2403.5 | Light brown, shiny | *Exophiala spinifera* | 33 | 33 |
| 2403.25 | Dark brown, shiny | *Exophiala spinifera* | 1 | 1 |
| 2043.12 | Brown, velvety | *Rhinocladiella atrovirens* | 4 | 4 |
| 2403.2 | Grey, velvety | *Rhinocladiella atrovirens* | 1 | 1 |
| Totals | | | 39 | 39 |

[1]Kernel source: Tifton, Georgia. Seed was split, washed in 5 ml sterile water and then 100 ul was plated onto YPD agar containing cycloheximide (500 mg/L) and chloramphenicol (50 mg/L).

From these results it was concluded that growth on fumonisin as the sole carbon source is the most reliable indicator of the ability to produce the fumonisin-degrading esterase.

The esterase isolated from *E. spinifera* was then subjected to other treatments, including proteases, to determine whether and how the enzyme would function in various environments. The results are indicated in Table 5.

TABLE 5

Effect of various treatments on modification of FB1

| Treatment | Conditions | FB1 Hydrolase activity* |
|---|---|---|
| Control | 16 hr, 37° C., pH 5.2 | +++ |
| Boiling water bath | 100° C., 30 min, pH 5.2 | − |
| Protease K | 0.01 mg/ml, 16 hr, 37° C., pH 5.2 | + |
| Pronase E | 0.01 mg/ml, 16 hr, 37° C., pH 5.2 | ++ |
| Chymotrypsin | 0.01 mg/ml, 16 hr, 37° C., pH 5.2 | ++ |
| Trypsin | 0.01 mg/ml, 16 hr, 37° C., pH 5.2 | +++ |
| EDTA | 50 mM | ++ |
| DTT | 25 mM | +++ |
| Ca$^{++}$ | 50 mM | +++ |
| Mg$^{++}$ | 50 mM | +++ |
| PMSF | 10 mM | +++ |

*10-fold concentrated, 11 to 15 day culture filtrates treated as described and then incubated with FB1 (0.5 mg/ml final conc) overnight at 37° C. Analysis by $C_{18}$ TLC/fluorescamine spray following overnight incubation at 37° C. with 1 mg/ml fumonisin
− = no hydrolysis

TABLE 5-continued

Effect of various treatments on modification of FB1

| Treatment | Conditions | FB1 Hydrolase activity* |
|---|---|---|

± = trace amounts of hydrolysis
+ = incomplete hydrolysis
++ = incomplete hydrolysis
+++ = complete hydrolysis Next, the pH range of activity of the fumonisin esterase was evaluated by measuring fumonisin degradation in the presence of citrate and citrate-phosphate buffers at varying pH levels. Results are shown in Table 6. From this, it was concluded that the pH range of the enzyme was quite wide, and that the enzyme would function at the internal pH of plants and plant cells.

TABLE 6

Effect of buffer pH on hydrolysis of fumonisin $B_1$ by *E. spinifera* culture filtrate

| Buffer | pH | FB1 Hydrolase activity* |
|---|---|---|
| 0.1 M citrate | 3.0 | +++ |
| 0.1 M citrate-phosphate | 4.0 | +++ |
| 0.1 M citrate-phosphate | 5.0 | ++ |
| 0.1 M citrate-phosphate | 6.0 | ++ |
| 0.1 M phosphate | 7.0 | ± |
| 0.1 M phosphate | 8.0 | − |

*reactions were carried out at 37° C. overnight and then assayed by TLC
*Analysis by $C_{18}$ TLC/fluorescamine spray following overnight incubation at 37° C. with 1 mg/ml fumonisin.
− = no hydrolysis
± = trace amount of hydrolysis
+ = incomplete hydrolysis
++ = incomplete hydrolysis
+++ = complete hydrolysis The fumonisin esterase isolated from *E. spinifera* and *R. atrovirens* was compared with other known esterases from various sources as supplied by commercial vendors. The results shown in Table 7 indicate that the fumonisin esterase is a unique enzyme that is highly specific in its activity and does not have a generalized esterase activity comparable to that of any of the known enzymes tested.

TABLE 7

Hydrolysis of fumonisin $B_1$ by commercial esterases and hydrolases

| Enzyme | Code | Source, purity | Units/mg prot. | Units per rxn | Assay pH | FB1 hydrolysis |
|---|---|---|---|---|---|---|
| Esterase, nonspecific | EC 3.1.1.1 | Rabbit | 100 | | 8.0 | − |
| Esterase, nonspecific | EC 3.1.1.1 | Porcine liver | 200 | | 7.5 | − |
| Lipase | EC 3.1.1.3 | *Candida cylindrica* | 35 | | 7.7 | − |
| Cholinesterase, butyryl | EC 3.1.1.8 | Horse serum, highly purified | 500 | 15 | 8.0 | − |
| Cholinesterase, acetyl | EC 3.1.1.7 | Bovine, partially pure | 0.33 | 0.15 | 8.0 | − |
| Cholesterol esterase | EC 3.1.1.13 | Bovine, partially pure | 0.5 | 0.15 | 8.0 | − |
| Cholesterol esterase | EC 3.1.1.13 | Porcine, partially pure | | 0.15 | 8.0 | − |

TABLE 7-continued

Hydrolysis of fumonisin $B_1$ by commercial esterases and hydrolases

| Enzyme | Code | Source, purity | Units/mg prot. | Units per rxn | Assay pH | FB1 hydrolysis |
|---|---|---|---|---|---|---|
| Cholesterol esterase | EC 3.1.1.13 | *Pseudomonas fluorescens* | 12 | 1.5 | 7.0 | − |
| Cholesterol esterase, | EC 3.1.1.13 | Pseudomonas sp. | 200 | 15 | 7.0 | ± |
| Acetylesterase | EC 3.1.1.6 | Orange Peel partially pure | 4 | 0.15 | 6.5 | − |
| Pectinesterase | EC 3.1.1.11 | Orange Peel, partially pure | 100 | 1.5 | 7.5 | − |
| Pectinase | EC 3.2.1.15 | Rhizopus Crude | 0.5 | 1.5 | 4.0 | − |
| Pectinase | EC 3.2.1.15 | Aspergillus Partially pure | 5 | 0.1 | 4.0 | − |
| Fumonisin esterase | ? | *Exophiala spinifera*, crude | unk | unk | 5.2 | +++ |

*Analysis by $C_{18}$ TLC/fluorescamine spray following overnight incubation at 37° C. with 1 mg/ml fumonisin.
− = no hydrolysis
± = trace amount of hydrolysis
+ = incomplete hydrolysis
++ = incomplete hydrolysis
+++ = complete hydrolysis The enzyme of this invention was evaluated for inducibility by growing an Exophiala culture on various carbon sources of varying degrees of structural similarity to fumonisin. The results, shown in Table 8, illustrate that both the original form of fumonisin and its metabolite are capable of inducing enzyme production, but that inducibility of the enzyme is also quite specific.

TABLE 8

Ability of various carbon sources to support growth and/or induction of FB1 hydrolytic activity Exophiala culture activity

| Carbon source | Concentration | Growth | FB1 hydrolase activity |
|---|---|---|---|
| FB1 | 0.1% | + | + |
| Alkaline hydrolyzed FB1 (AP1) | 0.1% | + | + |
| Na+ Tricarballylate | 0.1% | ± | − |
| Sphingosine | 0.1% | − | − |
| Phytosphingosine | 0.1% | − | − |
| Na+ Citrate | 0.1% | + | − |
| Sucrose | 0.1% | + | − |
| Glucose | 0.1% | + | − |

The ability of the fumonisin esterase to cleave other organic carboxylesters was also evaluated in comparison to its ability to hydrolyze fumonisin. The results, shown in Table 8, also illustrate that the enzyme hydrolyzed the tricarballylates of other related aminoalcohols such as $FB_2$ and AAL toxin.

TABLE 9

Hydrolysis of organic carboxylesters by Exophiala crude concentrated culture filtrate

| Substrate | Conditions | Assay method | Hydrolysis by Exophiala culture filtrate |
|---|---|---|---|
| FB1 | pH 5.2, 37° C., 1 hr | $C_{18}$ TLC: fluorescamine | + |
| FB2 | pH 5.2, 37° C., 1 hr | $C_{18}$ TLC: fluorescamine | + |
| AAL-toxin | pH 5.2, 37° C., 1 hr | $C_{18}$ TLC: fluorescamine | + |

Enzyme activity of culture filtrate and mycelium.

*Exophiala spinifera* isolate 2141.10 was grown on YPD agar for 1 week, and conidia were harvested, suspended in sterile water, and used at 105 conidia per ml to inoculate sterile Fries mineral salts medium containing 1 mg/ml purified FB1 (Sigma Chemical Co.). After 2 weeks incubation at 28° C. in the dark, cultures were filtered through 0.45 micron cellulose acetate filters, and rinsed with Fries mineral salts. Fungal mycelium was suspended in 15 mL of 0.1 MC-FB1, pH 5.2 +1 mM EDTA+3 µg/mL Pepstatin A+1.5 µg/mL Leupeptin and disrupted in a Bead Beater™ using 0.5 mm beads and one minute pulses, with ice cooling. Hyphal pieces were collected by filtering through Spinx(0.22 µm), and both mycelial supernatant and original culture filtrates were assayed for fumonisin modification by methods outlined above.

Preparation of crude culture filtrate.

Agar cultures grown as above were used to inoculate YPD broth cultures (500 ml) in conical flasks at a final concentration of 105 cells per ml culture. Cultures were incubated 5 days at 28° C. without agitation and mycelia harvested by filtration through 0.45 micron filters under vacuum. The filtrate was discarded and the mycelial mat was washed and resuspended in sterile carbon-free, low mineral salts medium (1 g/liter $NH_3NO_4$; 1 g/liter $NaH_2PO_4$; 0.5 g/liter $MgCl_2$; 0.1 g/liter NaCl; 0.13 g/liter $CaCl_2$; 0.02 g/liter $FeSO_4.7H_2O$, pH 4.5) containing 0.5 mg/ml alkaline hydrolyzed crude FB1. After 3–5 days at 28° C. in the dark with no agitation the cultures were filtered through low protein binding 0.45 micron filters to recover the culture filtrate. Phenylmethyl sulfonyl fluoride (PMSF) was added to a concentration of 2.5 mM and the culture filtrate was concentrated using an Amicon™ YM10 membrane in a stirred cell at room temperature, and resuspended in 50 mM sodium acetate, pH 5.2 containing 10 mM $CaCl_2$. The crude culture filtrate (approx. 200-fold concentrated) was stored at $-20°$ C.

To obtain preparative amounts of enzyme-hydrolyzed fumonisin, 10 mg. of FB1 (Sigma) was dissolved in 20 mL of 50 mM sodium acetate at pH 5.2+10 mM $CaCl_2$, and 0.25 mL of 200× concentrated crude culture filtrate of 2141.10 was added. The solution was incubated at 37° C. for 14 hours, and then cooled to room temperature. The reaction mixture was brought to approx. pH 9.5 by addition of 0.4 mL of 4 N KOH, and the mixture was extracted twice with 10 mL ethyl acetate. The combined organic layers were dried under $LN_2$ and resuspended in $dH_2O$. 2.5 milligrams of organic extracted material were analyzed by Fast Atom Bombardment (FAB) mass spectrometry, The resulting mass spectrum showed a major ion at M/z (+1)=406 mass units, indicating the major product of enzymatic hydrolysis was AP1 which has a calculated molecular weight of 405.

Additional characterization of fumonisin esterases from *Exophiala spinifera* and Gram-negative bacterium species.

Crude, concentrated culture filtrates (induced for FB1 esterase activity) from *E. spinifera* isolate 2141.10 and bacterium, ATCC 55552 sp. 2412.1 were chromatographed on a Pharmacia® Superdex 75 size exclusion column and eluted with 50 mM sodium phosphate, pH 6.0 containing 0.2 M NaCl. One-mL fractions were collected and assayed for FB1 esterase activity by methods described above. The retention times for the 2141.10 and 2412.1 FB1 esterases resulted in estimated molecular weights of 44.5 and 28.7 kilodaltons, respectively.

Similarly, crude concentrated culture filtrates in 1.7 M ammonium sulfate were injected onto a Pharmacia® Phenyl Sepharose FPLC column equilibrated with 1.7 M ammonium sulfate in 50 mM sodium phosphate pH 6.0 (Buffer A). A 30 mL, linear gradient of Buffer A to distilled water was applied, followed by a wash with 0.1% Triton X-100 in. 50 mM sodium phosphate, pH 6.0. One-mL fractions were collected and assayed for both FB1 esterase and for nonspecific esterase (as measured by napthyl acetate hydrolysis using the method of Dary et al. (1990) "Microplate adaptation of Gomori's assay for quantitative determination," *Journal of Economic Entomology* 83: 2187–2192. Both fungal and bacterial FB1 esterase activity eluted at approx. 0.4 M ammonium sulfate. Naphthyl acetate esterase activity was detected in both fungal and bacterial cultures but this activity did not co-elute with the FB1 esterase activity. Thus the fungal and bacterial FB1 esterases are not the same as nonspecific esterases detectable in the culture filtrates of these microbes.

EXAMPLE 2

Cloning of Bacterium ATCC 55552 Esterase Gene

The bacterium ATCC 55552 esterase gene was cloned in a lambda ZAP express expression library from Sau3A partially digested bacterial DNA (4–8 kb size selected from ATCC 55552). Pools of lambda lysates were tested for fumonisin esterase assay by TLC using pure fumonisin B1 as a substrate, and positive pools were sub-sampled to enrich for positive clones. Individual plaques were resuspended and activity assayed in the lysate. One positive clone was purified, phagemid excised and DNA prepared for sequencing. A 4 kilobase DNA fragment containing fumonisin esterase activity was sequenced and found to contain a 1589 base pair region containing a 529 amino acid open reading frame with high homology to members of the serine carboxylesterase type B superfamily (SEQ ID NO:11). The open reading frame codes for a protein (called BEST1, SEQ ID NO:12) with a putative signal peptide from amino acid 1 to 38, giving a mature protein with a calculated molecular weight of 51,495.63 daltons and a pI of 8.19. This open reading frame showed 52.5% similarity and 34% identity with the amino acid sequence of a rabbit cholinesterase (P37176). Other cholinesterases showed similar homology scores. The BEST1 sequence was also 53.0% similar and 36.4% identical to a Bacillus subtilis para-nitrobenzyl esterase (P04058). The open reading frame also showed 54.6% similarity and 34.9% identity with the *Exophiala spinifera* fumonisin esterase (Esp1). Aside from their overall similarity with other type B carboxylesterases, Esp1 and BEST1 share two short amino acid domains not found in other known esterases of this type:

| Protein | Sequence | From | To |
|---|---|---|---|
| BSP1 | ATLM | 292 | 295 |
| BEST1 | ATLM | 286 | 289 |
| ESP1 | TNI | 175 | 177 |
| BEST1 | TNI | 172 | 174 |

These domains may be involved in the substrate specificity of these enzymes (Cygler M., Schrag, J. D., Sussman, J. L. Harel, M., Silman I., Gentry, M. K. Doctor, B. P. (1993) Relationship between sequence conservation and 3-Dimensional structure in a large family of esterases, lipases, and related proteins. Protein Sci. 2:366–382.).

EXAMPLE 3

Preparation of AP1-Induced and Non-Induced Mycelium

*Exophiala spinifera* isolate 2141.10 was grown in YPD broth for days at 28° C., mycelium was harvested on 05. micron cellulose acetate filters and transferred to fresh medium consisting of Fries mineral salts (Gilchrist D G, Grogan R G (1976) "Production and nature of a host-specific toxin from *Alternaria alternata* f.sp. *lycopersici.*" *Phytopathology* 66: 165–171) amended with hydrolyzed fumonisin B1 (AP1) (0.5 mg/mL) or delta-aminobutyric acid (δ-ABA) (1 mg/mL) as the sole carbon source. Cultures were incubated in the dark for 48 hr at 28° C. and culture supernatants removed by filtration through 0.5 micron cellulose acetate. The remaining mycelial mat was washed with sterile Fries mineral salts and then frozen in liquid nitrogen for storage.

EXAMPLE 4

Cloning the Fumonisin Esterase Gene from *Exophiala spinifera*

The mycelial mats described above (~1 gram) were ground in liquid nitrogen in a mortar and pestle following addition of 10 ml, "TRIREAGENT" (Molecular Research Center, Inc. Cincinnati, Ohio) in the presence of 0.2 volume chloroform. The grindate was centrifuged and the resulting supernatant precipitated with isopropanol. The resulting pellet was extracted with phenol, ethanol precipitated, and stored at −80° C.

The RNA in water (0.4 mL) was enriched for poly-A-containing mRNA using biotin-oligo(dT) and a streptavidin magnetic bead system (Promega) using the manufacturer's instructions. The polyA(+)-enriched RNA was stored at −80° C.

First strand cDNA synthesis from polyA(+)-enriched RNA was carried out using M-MLV reverse transcriptase (37° C., 1 hr). The reaction mixture was extracted with phenol and chloroform. Aliquots were taken for polymerase chain reaction (PCR) using the degenerate primers identified in SEQUENCE I.D. NOS. 1 through 4:
ESP5'-OL1 GGGGAATTCGARGAYTGNYTNTAYNTNAAYRT (SEQUENCE I.D. NO. 1)
ESP5'-OL2 GGGGAATTCMCNGTNNTNVTNTGGATNYAYGGNGGNG (SEQUENCE I.D. NO. 2)
ESP3'-OL 1 GGGAAGCTTGGRTYNCCNCCRAANKBNGCDATRTT (SEQUENCE I.D. NO. 3)
ESP3'-OL2 GGGAAGCTTCNCCNGCNSWYTCNCCRAANADNGTNA (SEQUENCE I.D. NO. 4)
Most bases designated "N" were inosines.
Thermocycler reaction conditions were:
1. 94° C. 2 min
2. 94° C. 30 sec
45° C. 2 min
4. 72° C. 1 min
5. repeat steps 2–4 for 35×
6. 72° C. 5 min The cloned region contains an open reading frame with the partial protein or amino acid sequence
. . . SFHLYDGASFAANQDVIVVTINYRTNILGFPAAPQLPITQRNLGFLDQRFALDWVQRNIAAFGGDPRKVT FFGESA . . . (SEQUENCE I.D. NO. 5)

The above deduced amino acid sequence from DNA sequence showed significant homology to a family of proteins that includes cholinesterases, acetylcholinesterases, carboxylesterases, and certain lipases (Cygler M, Schrag J D, Sussman J L, Harel M, Silman I, Gentry M K, Doctor B P (1993) "Relationship between sequence conservation and 3-Dimensional structure in a large family of esterases, lipases, and related proteins." *Protein Sci* 2: 366–382.)

EXAMPLES 5–6

Comparison of Deduced Amino Acid Sequence to Known Sequences

In comparison with a sequence published in Arpagaus, M., Chatonnet, A., Masson, P., Newton, M., Vaughan, T. A., Bartels, C. F., Nogueira, C. P., La Du, B. N., and Lockridge, O. *J. Biol. Chem.* 266, 6966–6974 (1991), 43 of the 76 amino acids in ESP26-1 were identical to a dog pancreatic cholinesterase.

In another comparison 32 of 62 amino acids from ESP26-1 were identical to a fungal lipase, as published by Lotti, M., Grandori, R., Fusetti, F., Longhi, S., Brocca, S., Tramontano, A., and Alberghina, L., *Gene* 124: 45–55 (1993).

EXAMPLE 7

Northern Blot Analysis of Induced, Non-Induced *Exophiala spinifera*

Total RNA extracted from *Exophiala spinifera* cultures as described in the preceding examples was electrophoresed on agarose gels containing formaldeyde, blotted to nitrocellulose, and probed with random-primed 32P-labelled ESP26-1 cDNA. The probe hybridized to an RNA of approximately 2.0 kilobases in size in the induced lane, but not in the non-induced lane.

EXAMPLE 8

Isolation of Full Length cDNA of ESP26-1 from *Exophiala spinifera*

To obtain 3'-end of the cDNA coding for the putative esterase, a 3'-rapid amplification of cDNA ends protocol (3'-RACE) was employed (Frohman, M. A., Dush, M. K., and Martin, G. R. 1988 "Rapid production of full-length cDNAs from rare transcripts: Amplification using a single gene-specific oligonucleotide primer." *Proc. Natl. Acad. Sci. (USA)* 85: 8998–9002). 5 µg of total RNA isolated from AP1 induced *Exophiala spinifera*. mycelia was used as template for reverse transcription reaction. The reverse transcription reaction and subsequent PCR amplification was performed with a 3'-RACE kit (Gibco BRL). The gene-specific primer (ESP3'-1: GCTAGTTTCGCAGCCAATCA-GGA) (SEQUENCE I.D. NO. 6) was designed based on ESP26-1 sequence.
PCR reaction conditions were:
1. 94° C. 4 min
2. 94° C. 45 sec
3. 60° C. 25 sec
4. 72° C. 3 min
5. repeat steps 2–4 for 40×
6. 72° C. 10 min A resulting 1.5 kb DNA fragment was blotted to nitrocellulose and hybridized with cDNA ESP26-1 under highly stringent hybridization and wash conditions (last wash: 0.1×SSC, 0.5% SDS, 65° C. for 30 min.) The DNA fragment was gel-isolated, ligated into a pGEM-T vector (Promega), and transformed into DH5α (Gibco BRL). The resulting plasmid DNA (p3RC-2) was sequenced using M13 universal primer. Sequence comparison of 3RC-2 and ESP26-1 indicated the ESP26-1 overlapped 100% with the 5' end of 3RC-2 sequence.

To obtain the amino-terminal sequence, a 5'-RACE strategy was employed (Frohman, et al., supra). 5 µg of total RNA isolated from AP1 induced *Exophiala spinifera* mycelia was reverse transcribed with SuperScript I RNase H-reverse Transcriptase (Gibco BRL) using an anti-sense primer constructed against ESP26-1 sequence (ESP5'-1: AAAGGCTGCGATGTTCCGCTGTA) (SEQUENCE I.D. NO. 7). The cDNA was tailed with dATP using terminal transferase (Promega) and used as a template for nested amplification using a second gene-specific anti-sense primer (ESP5'-2: TCGCTGTGTTATTGGCAGCTGAG. (SEQUENCE I.D. NO. 8). C was a silent mutation of A in order to create a Pvu II restriction site) and an end-blocked polyT primer (BamT17V: CGCGGATCCGTTTTTTTTTTTTTTTV) (SEQUENCE I.D. NO. 9).
PCR reaction conditions were:
1. 94° C. 4 min
2. 94° C. 45 sec
3. 40° C. 45 sec
4. 60° C. 25 sec
5. 72° C. 3 min
6. repeat steps 2–5 for 41×
7. 72° C. 10 min The PCR products were fractionated on a 1.5% agarose gel. The amplified product was gel-isolated, ligated into pGEM-T (Promega), and transformed into DH5 (Gibco BRL). The resulting 5' RACE product was sequenced and shown to overlap as expected with the 3' RACE product and to contain an open reading frame with significant homology to members of the serine esterase/lipase superfamily described by Cygler et al. (supra). The overlapping sequences obtained by 3' RACE and 5' RACE were combined to yield a cDNA sequence corresponding to the complete open reading frame.

To isolate the entire cDNAs coding sequence for the putative mature fumonisin esterase, two PCR primers were designed based on the compiled sequences from 5'-RACE and 3'-RACE clones. The forward primer (FUMF2, sense strand, SEQ ID NO: 13) was:
5'-CATATGGCTAGCGCTCCTACTGTCAAGATTGAT-GCT-3',
and the reverse primer (FUMR, antisense strand, SEQ ID NO: 14) was:
5 '-GACGAGCTCCGCTGTAGGTACAATACCCGGGT-CCT-3'
(Underlined nucleic acid residues were derived from RACE clones coding for the fumonisin esterase). The PCR condition was as follows:
0.5 ml *E. spinifera* 1st strand of cDNA [primed with oligo(dT)]
0.4 ml 10 mM dNTP
2.0 ml 10×PCR buffer
0.5 ml Taq polymerase (5 units/ml)
0.5 ml FUMF2 primer (10 uM)
0.5 ml FUMR primer (10 uM)
15.6 ml HPLC grade water
(All reagents were purchased from Boehringer Mannheim Corp.)
PCR profile:
Step 1 94° C. 3 minutes
Step 2 94° C. 30 seconds
Step 3 60° C. 30 seconds
Step 4 72° C. 2 minutes
Step 5 go to Step 2 for 39 more times
Step 6 72° C. 10 minutes
Step 7 End Agarose gel electrophoresis analysis indicated a 1.5kb single DNA band was amplified with primer pair FUMF2/FUMR. The amplified DNA was gel purified and ligated to a pGEM-T vector (Promega Corp.). After transformation of the ligation mixture into *E. coli* DH5a competent cells, 36 colonies were picked and analyzed by PCR using FUMF2/FUMR primers. Four positive transformants were identified by this method. One of the four positive clones, named pGFUM29, was sequenced at both directions by primer walking method. Each strand was at least sequenced twice to ensure sequence accuracy. The full length, 1937 bp cDNA clone from *Exophiala spinifera* 2141.10 (abbreviated ESP1, SEQ ID NO: 15) contains an open reading frame of 537 amino acids as shown below (SEQUENCE I.D. NO. 10).

MPSRYILSWLLTCFLGIAFG-
SRCGSSAPTVKIDAGMVVGTTTTVPGT-
TATVSEFLGV
PFAASPTRFAPPTRPVPWSTPLQATAYGPACPQQF-
NYPEELREITMAWFNTPPPS- AG ESED-
CLNLNIYVPGTENTNKAVMVWIYGGA-
LEYGWNSFHLYDGASFAANQDVIVV
TINYRTNILGFPAAPQLPITQRNLGFLDQRFALDW-
VQRNI- AAFGGDPRKVTIFGQSA GGRSVDV-
LLTSMPHNPPFRAAIMESGVANYNFP-
KGDLSEPWNTTVQALNCTTSIDI
LSCMRRVDLATLMNTIEQLGLGFEYTLDNVTVV-
YRSETARTT- GDIARVPVLVGTVA NDGLLFVL-
GENDTQAYLEEAIPNQPDLYQTLLGAY-
PIGSPGIGSPQDQIAAIETEVRF QCPSAIV-
AQDSRNRGIPSWRYYYNATFENLELFPGSEVYH-
SSEVGMVF- GTYPVASA TALEAQTSKYMQ-
GAWAAFAKNPMNGPGWKQVPNVAALG-
SPGKAIQVDVSPATID QRCALYTHYYTELG-
TIAPRTF

This open reading frame (ORF) shows some homology to members of the serine esterase/lipase superfamily described by Cygler et al. (supra). The most extensive homology is 35.9% identity in 320 amino acid overlap with butyrylcholinesterase from *Oryctolagus cuniculus* (rabbit).

The deduced Esp1 protein contains a signal peptide which is cleaved at position 26/27 yielding a. mature protein with a calculated MW of 54953.781 and calculated pI of 4.5. These calculated values are consistent with the estimated MR and pI of the fumonisin esterase activity described above.

A comparison of the Esp1 open reading frame consensus regions in the esterase superfamily (Cygler et al., supra) reveals numerous conserved features indicating Esp1 may code for a serine esterase. The Esp protein has a potential serine active site consensus at 223–228; a putative aspartate active site consensus at 335–341 that is typical of cholesterol esterases and Drosophila 6 and P proteins [the majority of members of this superfamily, including fungal lipases and carboxylesterases have glutamate at the active site instead of aspartate]; and a putative histidine active site that is different from any members of the family, containing additional amino acids between the G and H. The putative Esp mature protein has a total of 6 cysteines, for 3 possible disulfide bridges, consistent with at least a subset of the esterases in the superfamily described by Cygler et al., supra.

Thus the Esp ORF has most of the hallmarks of a bona fide member of the lipase/esterase superfamily, including a putative active site triad and other conserved amino acids. The regions of conservation are not consistent with any one substrate subgroup (i.e. lipase, cholinesterase, carboxylesterase, or cholesterol esterase), but seem to be contain some features of several of these, and Esp appears to be unique among known esterases in its putative active site His consensus sequence.

EXAMPLE 9

Effect of FB1 and AP1 on Maize Coleoptiles

Maize coleoptiles from 4 day dark-grown germinated maize seeds were excised above the growing point and placed in 96-well microtiter plates in the presence of 60 microliters of sterile distilled water containing FB1 or AP1 at approximately equimolar concentrations of 1.5, 0.5, 0.15, 0.05, 0.015, 0.005, 0.0015, or 0.0005 millimolar, along with water controls. After 2 days in the dark at 28° C. the coleoptiles were placed in the light and incubated another 3 days. Injury or lack thereof was evaluated as follows:

| | 0 | .0005 | .0015 | .005 | .015 | .05 | .15 | .5 | 1.5 | mM |
|---|---|---|---|---|---|---|---|---|---|---|
| FB1 | – | – | – | – | +/– | + | + | + | + | |
| AP1 | – | – | – | – | – | – | – | – | + | |

+ = brown necrotic discoloration of coleoptile
– = no symptoms (same as water control)

The results (see table above) indicate there is at least a 30-fold difference in toxicity between FB1 and AP1 to maize coleoptiles of this genotype. This is in general agreement with other studies where the toxicity of the two compounds was compared for plant tissues: In Lemna tissues, AP1 was approx. 40-fold less toxic (Vesonder RF, Peterson RE, Labeda D, Abbas HK (1992) "Comparative phytotoxicity of the fumonisins, AAL-Toxin and yeast sphingolipids in Lemna minor L (Duckweed)." *Arch Environ Contam Toxicol* 23: 464–467.). Studies with both AAL toxin and FB1 in tomato also indicate the hydrolyzed version of the molecule is much less toxic (Gilchrist DG, Ward B, Moussato V, Mirocha CJ (1992) "Genetic and Physiological Response to Fumonisin and AAL-Toxin by Intact Tissue of a Higher Plant." *Mycopathologia* 117: 57–64.). In a recent report Lamprecht et al. also observed an approximate 100-fold reduction in toxicity to tomato by AP1 versus FB1 (Lamprecht S, Marasas W, Alberts J, Cawood M, Gelderblom W, Shephard G, Thiel P, Calitz J (1994) Phytotoxicity of fumonisins and TA-toxin to corn and tomato. *Phytopathology* 84: 383391.)

EXAMPLE 10

Effect of FB1 and AP1 on Maize Tissue Cultured Cells (Black Mexican Sweet, BMS)

FB1 or AP1 at various concentrations was added to suspensions of BMS cells growing in liquid culture medium in 96-well polystyrene plates. After 1 week the cell density in wells was observed under low power magnification and growth of toxin-treated wells was compared to control wells that received water. Growth of BMS cells was significantly inhibited at 0.4 micromolar FB1, but no inhibition was observed until 40 micromolar AP1. This represents an approximate 100-fold difference in toxicity to maize tissue cultured cells. Similarly Van Asch et al. (Vanasch M A J, Rijkenberg F H J, Coutinho T A (1992) "Phytotoxicity of fumonisin b1, moniliformin, and t-2 toxin to corn callus cultures." *Phytopathology* 82: 1330–1332) observed significant inhibition of maize callus grown on solid medium at 1.4 micromolar. AP1 was not tested in that study, however.

EXAMPLE 11

AP1 Catabolase Activity

A cell-free extract that contains the catabolase activity was obtained by subjecting substrate-induced *Exophiala spinifera* cells to disruption using a bead beater in sodium acetate buffer, pH 5.2, and recovering the cell-free supernatant by centrifugation and 0.45 micron filtration. Catabolic activity is assayed by incubating extracts with AP1 (hydrolyzed fumonisin B1 backbone) or 14C-labelled AP1 with the extract and evaluating by TLC on C18 silica. The product AP1-N1 has a lower Rf than AP1 and is detected either by radiolabel scan or by $H_2O_4$ spray/charring of the TLC plate. AP1 -$N_1$ does not react with the amine reagent, fluorescamine, that is routinely used to detect AP1 on TLC plates, suggesting that the amine group is missing or chemically modified. Activity is greater at 37° C. than at room temperature, but following 30 min. at 65° C. or 100° C. (no AP1 catabolic activity remained). Activity is maximal at pH 9. At pH 9, complete conversion to AP1-$N_1$ occurred in 30 minutes. Activity is retained by 30,000 dalton molecular weight cutoff membrane, but only partially retained by 100,000 dalton molecular weight cutoff membrane. Other amine-containing substrates were tested for modification by the crude extract. Fumonisin (with tricarboxylic acids attached) is not modified by the extract, indicating that hydrolysis must occur first for the catabolase to be active. Other long-chain bases (sphingosine, sphinganine, phytosphingosine) are apparently not modified by the crude catabolase, suggesting the enzyme(s) is specific for the fumonisin backbone. Preparative amounts of the product, tentatively named AP1-N1, have also been purified and analyzed by C13 nmr. The results indicate that $AP_1$-$N_1$ has a keto group at carbon 2 instead of an amine, consistent with an oxidative deamination by an amine oxidase or amine dehydrogenase. The c-13 nmr data also indicate that AP1-N1 spontaneously forms an internal hemiketal between C-1 and C-5, resulting in a 5-membered ring with a new chiral center at C-2. All other carbon assignments are as in AP1, thus AP1-N1 is a compound of composition $C_{22}H_{44}O_6$, FW 404. The product of either enzyme acting on fumonisin would not be expected to display any significant toxicity (although this has not been tested).

EXAMPLE 12

Transformation and Regeneration of Maize Callus

Immature maize embryos from green house donor plants were bombarded with a plasmid (pPHP7649) containing the mature ESP1 gene (amino acid 27 to 525) fused to the barley alpha amylase signal sequence (Rahmatullah, et al., supra) operatively linked to the ubiquitin promoter or a plasmid (pPHP7650) containing the ESP1 gene with the ESP1 signal sequence operatively linked to the ubiquitin promoter plus a plasmid containing the selectable marker gene, PAT, (Wohlleben,W., Arnold,W., Broer,I., Hillemann,D., Strauch, E. and Puehler,A. "Nucleotide sequence of the phosphinothricin N-acetyltransferase gene from Streptomyces viridochromogenes Tue494 and its expression in Nicotiana tabacum" *Gene* 70, 25–37 (1988)) that confers resistance to the herbicide Bialophos by the following method:

Please note: All media recipes are in the Appendix.

Preparation of target tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate. These are cultured on 560L medium 4 days prior to bombardment, in the dark. The day of bombardment, the embryos are transferred to 560Y medium for 4 hours, arranged within the 2.5 cm target zone.

Preparation of DNA:

100 ul prepared tungsten particles in water 10 ul (1 ug) DNA in Tris EDTA buffer (1 ug total)

| 100 ul | 2.5M CaCl2 |
| 10 ul | 0.1M spermidine |

Each reagent is added sequentially to the tungsten particle suspension, while maintained on the multi-tube vortexer. The two plasmids are adjusted for a final 1:1 ratio by size. The final mixture is sonicated briefly, and allowed to incubate under constant vortexing for ten minutes. After the precipitation period, the tubes are centrifuged briefly, liquid removed, washed with 500 ml 100% ethanol, and centrifuged 30 seconds. Again the liquid is removed, and 105 ul 100% ethanol added to the final tungsten particle pellet. For particle gun bombardment, the tungsten/DNA particles are briefly sonicated and 10 ul spotted onto the center of each macro-carrier and allowed to dry about 2 minutes before bombardment.

Particle Gun Treatment:

The sample plates are bombarded at level #4 in particle gun #HE34-1or #HE34-2. All samples receive a single shot at 650 PSI, with a total of ten aliquots taken from each tube of prepared particles/DNA.

Subsequent treatment:

Following bombardment, the embryos are kept on 560Y medium for 2 days then transferred to 560R selection medium containing 3 mg/liter Bialophos, and sub-cultured every 2 weeks. After approximately 10 weeks of selection, selection-resistant callus clones are sampled for PCR and fumonisin esterase TLC activity analysis. Positive lines are transferred to 288J medium to initiate plant regeneration. Following somatic embryo maturation (2–4 weeks), well-developed somatic embryos are transferred to 272V medium for germination and transferred to the lighted culture room. Approximately 7–10 days later, developing plantlets are transferred to 272V medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

EXAMPLE 13

Demonstration of Functional Esterase Activity

Demonstration of esterase activity was accomplished by expressing the *E. spinifera* cDNA in two heterologous systems (an insect cell/baculovirus expression system, and transgenic maize obtained by microprojectile bombardment) and subsequently detecting fumonsin esterase activity in transformed cells. Similar results were obtained with insect cells infected with a baculovirus expression vector containing the esterase clone and transgenic maize cells. Both fungal and bacterial esterases retain their fumonisin hydrolytic activity when expressed in transgenic maize or the baculovirus expression system.

Fifty-eight transformed callus lines containing the ESP1 gene (with native or BAA signal sequence), produced as described above, plus 5 negative controls (50 mg fresh wt per line) were homogenized in 200 ul 150 mM sodium acetate pH 5.9 containing 5 mM CaCl2, 0.1% Tween-20, 5 mM leupeptin and 10 ug/ml pepstatin. The homogenates were ; centrifuged at 4000 rpm at 4 C, and 200 ul supernatant removed and stored frozen at −20 until assay. Supernatants were adjusted to equivalent Bradford protein (0.47 mg/ml) and assayed by thin layer chromatography (TLC) for $^{14}$C FB1 hydrolysis as follows:

1. Sample is spotted on a 10×5 cm C18 TLC plate (Whatman KC18)
2. After sample spots are dry, plate is developed in methanol:4%aqueous KCl (3:2).
3. Plate is removed from developing tank
4. For $^{14}$C experiments, plate is exposed to X-ray film for 1–7 days, or exposed to Molecular Dynamics phosphorimager plate for 12–48 hrs and viewed with Imagequant imaging software on a computer. In some experiments the plates were scanned with an AMBIS radiometric scanner connected to an IBM PC, and TIFF files of the scans generated from the AMBIS imaging software.
5. For amine spray: Spray developed plate (before it dries out) with 0.1 M sodium borate (pH 8 to 9). As soon as excess borate solution droplets have disappeared, spray with fluorescamine solution (0.4 mg/ml in acetonitrile) to saturation.
6. After 1 minute, spray plate with 0.01 M boric acid: acetonitrile (40:6)
7. Plate is dried at room temperature and examined under long wave UV light (using one or two hand-held UV light sources on either side of plate). The reaction relies on the reaction of the free amine of fumonisin with flourescamine under alkaline conditions, and the ability of the resulting adduct to fluoresce at low pH. Only molecules with a free amino group will be detected by this method. Sensitivity limit is less than 0.1 microgram.

FIG. 1 shows scan of a TLC plate on which callus extracts were chromatographed after 30 min incubation with $^{14}$C FB1 at 37 C. Relative positions for FB1, AP1, and tricarballylate or propanetricarboxylic acid (PTCA) are indicated. Asterisks denote esterase positive lines. The ESP1 protein was also detected by Western blot analysis (Towbin, H., Staehelin, T., & Gordon, J., *PNAS* (1979), 76:4350; Anderson, N. L., Nance, S. L., Pearson, T. W., & Anderson, N. G., *Electrophoresis* (1982), 3:135 and herein incorporated by reference) in extracts from transformed callus. The blot was probed with ESP1 antisera obtained from synthetic peptides based on ESP1 amino acid sequence (amino acids 98–115, 406–422, and 510–527). FIG. 1 and Western blot analysis clearly demonstrate that the ESP1 protein can be transformed into maize callus and expressed.

Once the transformed callus was found to express the ESP 1 gene, whole plants were regenerated as described above. Transformation of each plant can be confirmed using Southern blot analysis of genomic DNA. (Clark, M. (Ed.) *Plant Molecular Biology—A Laboratory Manual* (1997) Springer-Verlag) Typically, total DNA is isolated from each transformant. The DNA is then digested with restriction enzymes, fractionated in 1% agarose gels and transferred to nylon filters (e.g., HYBOND-N, Amersam) according to standard techniques. The blot is then probed with the gene of interest labeled with $^{32}$P. FIG. 2 shows Southern blots of six T0 families transformed with the fungal esterase gene, either in its native form or fused to the barley alpha amylase leader sequence. Integration patterns ranged form complex (e.g. 197499, 198271, 203029) to relatively simple (197637, 198231). One family (198189) showed no presence of the transgene.

To confirm that the T0 plants were expressing the ESP1 gene, maize leaf strips (1×4 cm) from T0 plants were imbibed with $^{14}$C-FB1 (1 mg/ml) for 72 hours at 21 degrees C. The central ¼ of each strip was extracted with 50% acetonitrile, centrifuged, and 2 ul spotted on $C_{18}$ TLC plates, as discussed above, along with FB1 and AP1 controls. (See FIG. 3) In lanes 5–6 there was apparent further metabolism of AP1. In addition T0 seed was tested for FB1 esterase activity. To compare callus expression to leaf expression, samples of both leaf and callus were analyzed by TLC. Thirty minute or 4 hour reactions were spotted on TLC plates (C18) and developed with MeOH:4% KC1 (3:2). Plates were scanned with a radiometric scanner (AMBIS) and scored for fumonisin esterase activity on a product), ++(up to 50% conversion to product) and +++(between 90–100% conversion to product).

Results were as follows:

| SAMPLE | CALLUS SCORE (30 MIN) | 30 MIN. LEAF SCORE | 4 HR. LEAF SCORE |
|---|---|---|---|
| A1 | + | − | − |
| B1 Control | − | − | − |
| C1 | ++ | − | − |
| D1 | + | − | + |
| E1 Control | − | − | − |
| F1 | +++ | + | ++ |

-continued

| SAMPLE | CALLUS SCORE (30 MIN) | 30 MIN. LEAF SCORE | 4 HR. LEAF SCORE |
|---|---|---|---|
| G1 | +++ | + | +++ |
| H1 | ++ | + | ++ |
| A2 | + | – | – |
| B2 Control | – | – | – |
| C2 Control | – | – | – |
| D2 | +++ | +++ | +++ |
| E2 | ++ | + | ++ |
| F2 | – | – | – |
| G2 | +++ | + | +++ |
| H2 | +++ | + | +++ |

In summary, 8 to 12 callus expressors were positive for leaf expression. All negative controls plus four callus expressors were negative. Of the four "+++" callus expressors, only one (D2) had the same high level (30 min. assay), but all were positive. A similar result was obtained with transgenic maize plants of inbred PHN46 (U.S. Pat. No. 5,567,861 and hereby incorporated by reference) that were transformed with the bacterial esterase clone BEST1 (SEQ ID NO: 11) in a similar plant expression vector.

Figure 4:
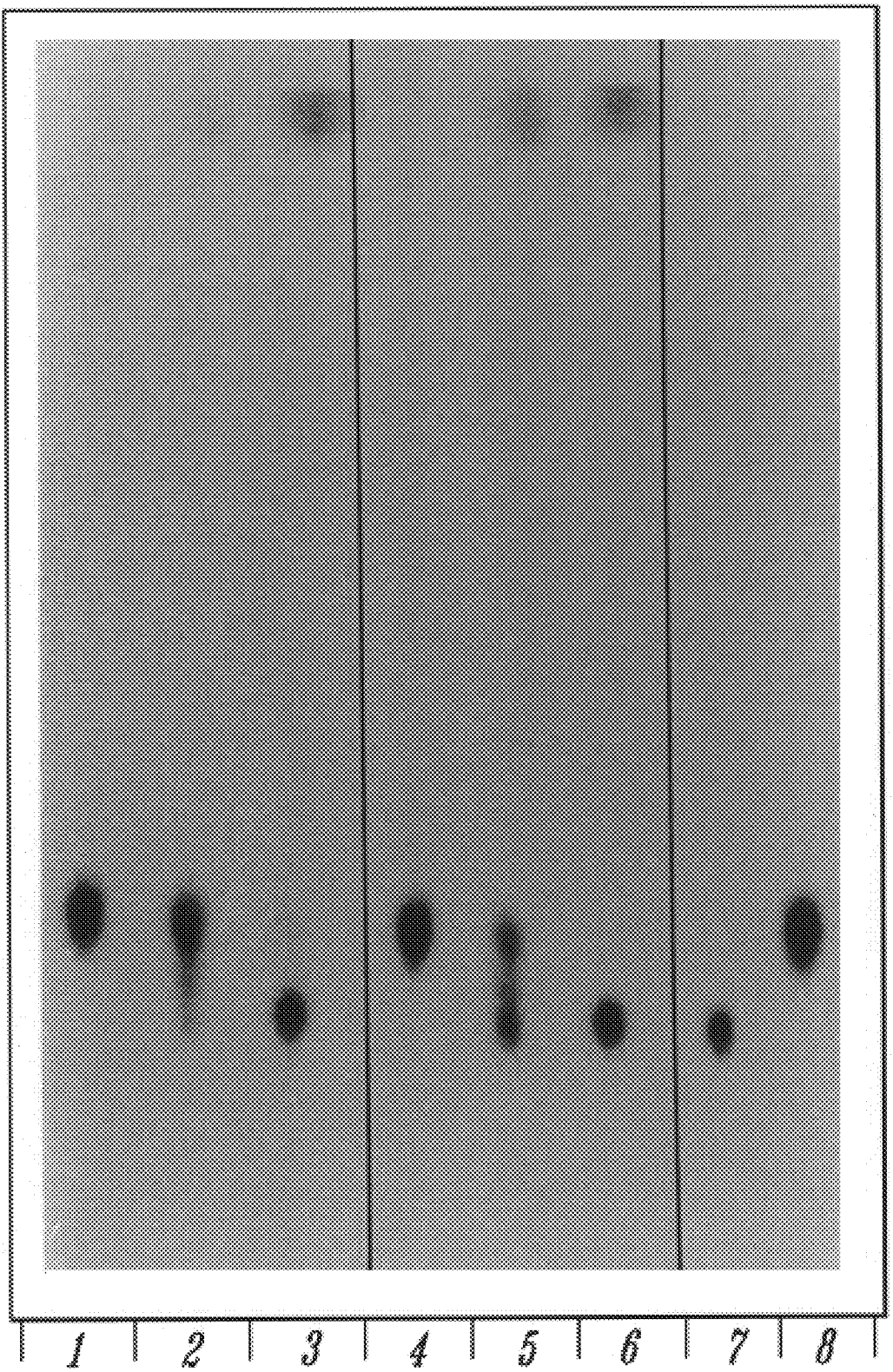
FIG. 4 demonstrates fumonisin esterase activity in aqueous extracts of mature seed from T0 plants transformed with ESP 1.
Figure 5:
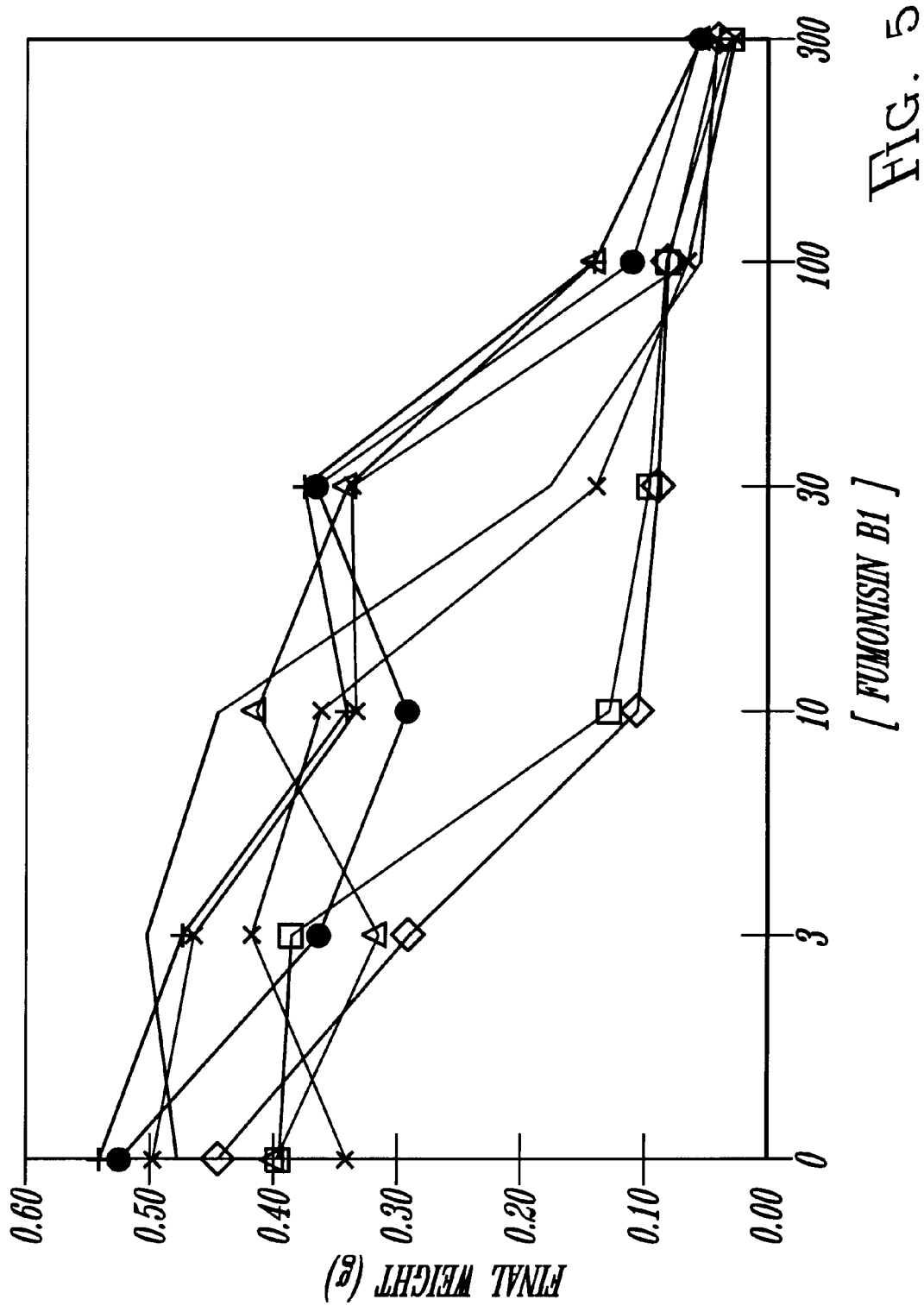
FIG. 5 shows a graph of survival rates of maize callus cells transformed with an expression vector containing the ESP1 gene and of maize callus without the expression vector on media containing fumonisin B1.

To study expression in seed, mature transformed seed was homogenized in 200 ul 150 mM sodium acetate pH 5.9 containing 5 mM CaCl2, 0.1% Tween-20, 5 mM leupeptin and 10 ug/ml pepstatin, centrifuged, and equal volumes of crude extract and $^{14}$C FB1 (1 mg/ml in same buffer minus tween, leupeptin, and pepstatin) were incubated at 37 C for 10 min for 1 hr, then spotted on TLC plates as described above. The results shown in FIG. 4, confirm that the ESP1 protein is expressed in seeds. Thus, fumonisn esterase can be used to transform maize plants and will express in the leaves and seeds of the plant.

EXAMPLE 14

Detoxification of Harvested Grain, Silage, or Contaminated Food Crop

The present invention also relates to a method of detoxifying a fumonisin or a structurally related mycotoxin with an enzyme having the structure of the fumonisin degradative enzymes or the AP1 catabolase elaborated by *Exophiala spinifera*, ATCC 74269, *Rhinocladiella atrovirens*, ATCC 74210, or the bacterium of ATCC 55552 during the processing of grain for animal or human food consumption, during the processing of plant material for silage, or food crops contaminated with a toxin producing microbe, such as but not limited to, tomato. Since the atmospheric ammoniation of corn has proven to be an ineffective method of detoxification (see B. Fitch Haumann, "Eradicating Mycotoxin in Food and Feeds," *INFORM* 6:248–257 (1995)), such a methodology is particularly critical where transgenic detoxification is not applicable.

In this embodiment, the fumonisin degradative esterase enzyme and/or the AP1 catabolase found in *Exophiala spinifera*, ATCC 74269, *Rhinocladiella atrovirens*, ATCC 74210, or the bacterium of ATCC 55552, are presented to grain, plant material for silage, or a contaminated food crop, or during the processing procedure, at the appropriate stages of the procedure and in amounts effective for detoxification of fumonisins and structurally related mycotoxins. Detoxification by this method can occur not only during the processing, but also any time prior to feeding of the grain or plant material to an animal or incorporation of the grain or food crop into a human food product, or before ingestion of the food crop.

The enzymes can be introduced during processing in appropriate manners, for example as a wash or spray, or in dried or lyophilized form or powered form, depending upon the nature of the milling process and/or the stage of processing at which the enzymatic treatment is carried out. See generally, Hoseney, R. C., *Principles of Cereal Science and Technology*, American Assn. of Cereal Chemists, Inc., 1990 (especially Chapters 5, 6 and 7); Jones, J. M., *Food Safety*, Eagan Press, St. Paul, Minn., 1992 (especially Chapters 7 and 9); and Jelen, P., *Introduction to Food Processing*, Restan Publ. Co., Reston, Va., 1985. Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The esterase from *Exophilia spinifera*, ATCC 74269, showed a range of activity from about pH 3 to about pH 6, and the esterase from the bacterium of ATCC 55552 showed a range of activity from about pH 6 to about pH 9.

Activity of fumonisin esterase T1 seed (the result of fertilizing T0 silks with pollen from an ear mold-susceptible inbred line) from six T0 plants representing 4 separate transformation events were planted in flats (approx. 30 seeds per T0). The resulting seedlings were assayed individually for fumonisin esterase activity by taking leaf punches and evaluating aqueous extracts for fumonisin esterase activity by a radiolabel TLC assay. As expected, most families showed an approximately 1:1 segregation for presence of the transgene. Equal numbers of esterase positive (+) and negative (−) plants from each family were transferred to pots and grown to maturity in a greenhouse. The seedlings had been infected with a mixed inoculum consisting of three pathogenic isolates of *Fusarium moniliforme* (MO33, MO35, and MO42) by placing a toothpick colonized with fungal mycelium next to each seed. Ear shoots were fertilized with pollen from Pioneer inbred PHN46 (U.S. Pat. No. 5,567,861 and hereby incorporated by reference). Developing ears were inoculated with the same three *F. moniliforme* isolates by placing a plastic bag containing Fusarium inoculum on filter paper over the ear.

Ears were harvested at maturity, dried to uniform moisture, and shelled. Approximately 5 grams of seed from each ear was ground in a spice grinder and the powder extracted with 50% acetonitrile according to standard protocols for fumonisn extraction (Rice, L. G., and Ross, P. F., Methods for detection and quantitation of fumonisins in corn, cereal products and animal excreta, *J Food Protect,* 57, 536 (1994); Plattner, R. D., Weisleder, D., and Poling, S. M., Analytical determination of fumonisins and other metabolites produced by *Fusarium moniliforme* and related species on corn, in Fumonisins in Food, Jackson, L. S., Devries, J. W., and Bullerman, L. B., Eds., Plenum Press Div Plenum Publishing Corp, 233 Spring St/New York/N.Y. 10013, pp. 57 (1996), and herein incorporated by reference). Fumonisin and hydrolyzed fumonisin levels in each batch extract were measured by LC-mass spectrometry. Table 10 shows the FB1 and AP1 levels detected in esterase (+) versus (−) seed, averaged across all transformation events. AP1 levels were extremely low in the esterase (−) samples, but were quite high in the esterase (+) sample population, indicating that the esterase gene is effective in hydrolyzing fumonisin produced in planta by a pathogenic Fusarium. Accordingly, even though the kernels on each ear were not uniformly expressing esterase activity in the germ (since they were produced from outcrossed, hemizygous maternal tissue), we also detected a strikingly lower average fumonisin level in the bulked esterase (+) ear tissue than in the esterase (−) ear tissue (see Table 10). Thus the esterase transgene can lower the average amount of fumonisin present in Fusarium-infected, harvested grain. An even more dramatic reduction in fumonisin can be obtained if the parent tissue is homozygous for the esterase gene. A similar result can be expected in other tissues of the maize plant that accumulate fumonisin, or in another plant species such as tomato which can be infected by a fungus producing a fumonisin analog like AAL toxin.

TABLE 10

FB1 and AP1 (hydrolyzed fumonisin) levels in transgenic seed from greenhouse-grown, Fusarium-inoculated maize plants.

| | ESP(+) plants | ESP(−) plants |
|---|---|---|
| AP1 in seed (ppm), average | 1.449 | 0.018 |
| FB1 in seed (ppm), average | 0.379 | 1.522 |
| Total Number of Plants | 56 | 56 |

EXAMPLE 15

Genetic Engineering of Ruminal Microorganisms

Ruminal microorganisms can be genetically engineered to contain and express either the fumonisin degrading enzymes or the AP1 catabolase elaborated by *Exophilia spinifera*, ATCC 74269, *Rhinocladiella atrovirens*, ATCC 74270, or the bacterium of ATCC 55552, or a combination of the enzymes. The genetic engineering of microorganisms is now an art recognized technique, and ruminal microorganisms so engineered can be added to feed in any art recognized manner, for example as a probiotic or inoculant. In addition, microorganisms capable of functioning as bioreactors can be engineered so as to be capable of mass producing either the fumonisin degrading esterases or the AP1 catabolase found in *Exophilia spinifera*, ATCC 74269, *Rhinocladiella atrovirens*, ATCC 74270, or the bacterium of ATCC 55552.

EXAMPLE 16

Use of Fumonisin Esterase as a Selectable and Scorable Marker

The esterase can be used for quantitative evaluation of gene expression using promoter fusions. A promoter of interest is fused to esterase and used in stable or transient transformation of plant cells using methods well known in the art. To synthesize the substrate for a hydrolyzable scorable marker, tricarballylic acid (TCA) is esterified to 5-bromo-3-indole using methods similar to those used to develop fumonisin analogs (Kraus, G. A., Applegate, J. M., and Reynolds, D., Synthesis of analogs of Fumonisin-B1, *J Agr Food Chem,* 40, 2331 (1992).; Lagu, B., Menaldino, D., Merrill, A. H. J., and Liotta, D., Synthesis of fumonisin analogs, 204*th American Chemical Society National Meeting*, Washington, D.C., USA, August, 204 (1992), and hereby incorporated by reference). Other esters can also be synthesized, including umbelliferyl, naphthyl, and flurorescein. A specific example of a fluorescent marker is fluorescein diacetate, which does not fluoresce until nonspecific esterases in living cells cleave the ester bonds giving rise to free fluorescein (Yang, H. C., Nemoto, Y., Homma, T., Matsuoka, H., Yamada, S., Sumita, O., Takatori, K., and Kurata, H., Rapid viability assessment of spores of several fungi by an ionic intensified fluorescein diacetate method, *Curr Microbiol,* 30, 173 (1995), and hereby incorporated by reference). Unlike the acetate ester, hydrolysis of tricarballylate esters by nonspecific esterases is minimal, resulting in very low background. In practice, the fumonisin ester is added to cells whose promoter activity is to be evaluated, and the amount of hydrolysis of tricarballylate in the presence of the fumonisin esterase is evaluated by fluorescence spectrometry or other visual evaluation, which will depend on the marker used.

In still another strategy tricarballylate is esterified to a toxin or herbicide by methods similar to those referenced above, giving rise to a protoxin or proherbicide that is inert and nontoxic until hydrolyzed by fumonisin esterase. An example is the herbicide phosphinothricin (glufosinate) or 2-Amino-4-(Hydroxymethylphosphinyl)-, Monoammonium Salt, (Zeiss, H-J, "Enantioselective synthesis of both enantiomers of phosphinothricin via asymmetric hydrogenation of alpha-acylamido acrylates". *Journal Of Organic Chemistry* 56(5): 1783–1788 (1991)), which can be esterified at the free carboxyl group or amine to tricarballylate, giving rise to an inactive form of the herbicide similar to that produced by the gene phosphinothricin N-acetyl transferase (Botterman-J; Gossele-V; Thoen-C; Lauwreys-M, "Characterization of phosphinothricin acetyltransferase and carboxyl-terminal enzymatically active fusion proteins". *Gene* (Amsterdam) 102(1): 33–38 (1991)). The tricarballylate ester of phosphinothricin is cleaved selectively and specifically by fumonisin esterase giving rise to the active herbicide. Only cells producing esterase will be inhibited by the proherbicide.

Plant callus is unable to grow in the presence of fumonisin, Therefore the fumonisin esterase gene can be used as a selectable marker by allowing only transformed cells expressing a fumonisin degradative enzyme to survive in the presence of fumonisin. The fumonisin esterase gene, ESP1, with the barley alpha amylase (BAA) signal sequence was bombarded into maize embryos as described in Example 13. When the transformed callus was placed on 560R selection medium without Bialaphos but containing 0–30 mg/l of fumonisin B1, a subpopulation of transformed cells were able to maintain or increase their weight as can be seen in FIG. 5. Lines A− and B− were two callus lines without the ESP1 construct. A and B lines with the + after characterize the level of expression of the enzyme. For example, A+ has a lower expression of the enzyme than A++. Control embryos not bombarded with the ESP1 construct were unable to proliferate and lost weight due to cell death.

In still another strategy, the tricarballylate group is esterified to a phytohormone such as indolebutyric acid (IBA), which is required in its free form for plant tissue culture cell growth in culture. This may be done by introducing a hydroxyl group into various positions of the benzene portion of the indole (Fuji-M; Muratake-H; Natsume,M, Preparation of alkyl-substituted indoles in the benzene portion: Part 6. Synthetic procedure for 4-, 5-, 6-, or 7-alkoxy- and hydroxy-indole derivatives.Chemical & Pharmaceutical Bulletin (Tokyo) 40(9): 2344–2352 (1992)). The hydroxy IBA derivatives are tested to determine which derivative is most similar to IBA in biological activity, and this positional isomer is esterified to tricarballylate by methods referenced earlier. Plant cells are transformed by any one of a number of methods, using a plant expression vector containing the fumonisin esterase gene driven by a constitutive promoter, typically including a second gene or genes of interest on its own promoter. The tricarballylate ester of hydroxy-IBA is added to a mineral salts and sucrose-based medium, at a concentration approximately equivalent to the concentration of IBA or hydroxy-IBA normally required for cell growth, and transformed cells are plated onto the medium. Only the cell which can hydrolyze the phytohormone ester can grow and proliferate, and so can be effectively selected from the mass of untransformed cells.

In all cases, the ester bond breakage by the fumonisin esterase results in increased activity such as fluorescence (fluorescein), a color reaction combined with precipitation (indole), or biological activity (IBA or fumonisin degradation). Tricarballylic acid released by hydrolysis remains in solution and is not metabolized by the cell; it is unlikely to be toxic at the concentrations used.

APPENDIX

| Ingredient | Amount | Unit |
|---|---|---|
| D-I H2O | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine .HCL 0.4 mg/ml | 0.500 | ml |
| L-Proline | 1.980 | g |
| Casein Hydrolysate (acid) | 0.300 | g |
| Sucrose | 20.000 | g |
| Glucose | 0.600 | g |
| 2, 4-D 0.5 mg/ml | 1.600 | ml |
| Gelrite @ | 2.000 | g |
| Dicamba 1 mg/ml # | 1.200 | ml |
| Silver Nitrate 2 mg/ml # | 1.700 | ml |

Directions:
@ = Add after bringing up to volume
= Add after sterilizing and cooling to temp.
Dissolve ingredients in polished D-I H2O in sequence
Adjust to pH 5.8
Bring up to volume with polished D-I H2O after adjusting pH
Sterilize and cool to 60° C.
= Dissolve 1.660 g of Calcium Chloride Dihydrate in 950.000 ml of polished D-I H2O. Then dissolve 4.629 of Ammonium Sulfate; 4.000 g of Potassium Phosphate Monobasic KH2PO4; 1.850 g of Magnesium Sulfate 7-H2O, MgSO4, 7H2O; and 28.300 g of Potassium Nitrate into sequence. Bring up to volume with polished D-I H2O.
= Dissolve 3.000 g of Boric Acid; 10.000 g of Manganous Sulfate Monohydrate; 0.250 g of Sodium Molybdate Dihydrate; and 0.750 g of Potassium Iodide in polished D-I H2O in sequence. Bring up to volume with polished D-I H2O.
= Dissolve 3.700 g of Disodium EDTA Dihydrate and 2.790 g of Ferrous Sulfate 7-Hydrate into D-I H2O. Bring up to volume with D-I H2O.
Total Volume (L) = 1.00

| Ingredient | Amount | Unit |
|---|---|---|
| H2O | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine .HCL 0.4 mg/ml | 0.500 | ml |

-continued

| Ingredient | Amount | Unit |
|---|---|---|
| L-Proline | 1.980 | g |
| Casein Hydrolysate (acid) | 0.300 | g |
| Sucrose | 20.000 | g |
| Glucose | 0.600 | g |
| 2, 4-D 0.5 mg/ml | 1.600 | ml |
| Gelrite @ | 2.000 | g |
| Dicamba 1 mg/ml # | 1.200 | ml |
| Silver Nitrate 2 mg/ml # | 1.700 | ml |
| Bialaphos 1 mg/ml # | 3.000 | ml |

Directions:
@ = Add after bringing up to volume
= Add after sterilizing and cooling to temp.
Dissolve ingredients in polished D-I H2O in sequence
Adjust to pH 5.8
Bring up to volume with polished D-I H2O after adjusting pH
Sterilize and cool to 60° C.
= Dissolve 1.660 g of Calcium Chloride Dihydrate in 950.000 ml of polished D-I H2O. Then dissolve 4.629 of Ammonium Sulfate; 4.000 g of Potassium Phosphate Monobasic KH2PO4; 1.850 g of Magnesium Sulfate 7-H2O, MgSO4, 7H2O; and 28.300 g of Potassium Nitrate into sequence. Bring up to volume with polished D-I H2O.
= Dissolve 3.000 g of Boric Acid; 10.000 g of Manganous Sulfate Monohydrate; 0.250 g of Sodium Molybdate Dihydrate; and 0.750 g of Potassium Iodide in polished D-I H2O in sequence. Bring up to volume with polished D-I H2O.
= Dissolve 3.700 g of Disodium EDTA Dihydrate and 2.790 g of Ferrous Sulfate 7-Hydrate into D-I H2O. Bring up to volume with D-I H2O.
Total Volume (L) = 1.00

| Ingredient | Amount | Unit |
|---|---|---|
| D-I H2O | 900.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine .HCL 0.4 mg/ml | 0.500 | ml |
| Sucrose | 20.000 | g |
| Glucose | 0.600 | g |
| 2, 4-D 0.5 mg/ml | 1.600 | ml |
| Gelrite @ | 2.000 | g |
| Dicamba 1 mg/ml # | 1.200 | ml |
| Silver Nitrate 2 mg/ml # | 0.425 | ml |
| Bialaphos 1 mg/ml # | 3.000 | ml |

Directions:
@ = Add after bringing up to volume
= Add after sterilizing and cooling to temp.
Dissolve ingredients in polished D-I H2O in sequence
Adjust to pH 5.8
Bring up to volume with polished D-I H2O after adjusting pH
Sterilize and cool to 60° C.
= Dissolve 1.660 g of Calcium Chloride Dihydrate in 950.000 ml of polished D-I H2O. Then dissolve 4.629 of Ammonium Sulfate; 4.000 g of Potassium Phosphate Monobasic KH2PO4; 1.850 g of Magnesium Sulfate 7-H2O, MgSO4, 7H2O; and 28.300 g of Potassium Nitrate into sequence. Bring up to volume with polished D-I H2O.
= Dissolve 3.000 g of Boric Acid; 10.000 g of Manganous Sulfate Monohydrate; 0.250 g of Sodium Molybdate Dihydrate; and 0.750 g of Potassium Iodide in polished D-I H2O in sequence. Bring up to volume with polished D-I H2O.
= Dissolve 3.700 g of Disodium EDTA Dihydrate and 2.790 g of Ferrous Sulfate 7-Hydrate into D-I H2O. Bring up to volume with D-I H2O.
Total Volume (L) = 1.00

| Ingredient | Amount | Unit |
| --- | --- | --- |
| D-I H2O | 800.000 | ml |
| CHU (N6) Basal Salts (SIGMA C-1416) | 1.600 | g |
| N6 Macronutrients 10X Stock ## | 60.000 | ml |
| Potassium Nitrate | 1.680 | g |
| B5H Minor Salts 1000X ### | 0.600 | ml |
| B5H Fe Na EDTA 100X #### | 6.000 | ml |
| Eriksson's Vitamin Mix (1000X SIGMA-1511) | 0.400 | ml |
| S & H Vitamin Mixture 100X Stock (S3766) | 6.000 | ml |
| Thiamine .HCL 0.4 mg/ml | 0.500 | ml |
| L-Proline | 1.980 | g |
| Casein Hydrolysate (acid) | .300 | g |
| Sucrose | 120.000 | g |
| Glucose | 0.600 | g |
| 2, 4-D 0.5 mg/ml | 1.600 | ml |
| Gelrite @ | 2.000 | g |
| Dicamba 1 mg/ml # | 1.200 | ml |
| Silver Nitrate 2 mg/ml # | 1.700 | ml |

Directions:
@ = Add after bringing up to volume
= Add after sterilizing and cooling to temp.
Dissolve ingredients in polished D-I H2O in sequence
Adjust to pH 5.8
Bring up to volume with polished D-I H2O after adjusting pH
Sterilize and cool to 60° C.
= Dissolve 1.660 g of Calcium Chloride Dihydrate in 950.000 ml of polished D-I H2O. Then dissolve 4.629 of Ammonium Sulfate; 4.000 g of Potassium Phosphate Monobasic KH2PO4; 1.850 g of Magnesium Sulfate 7-H2O, MgSO4, 7H2O; and 28.300 g of Potassium Nitrate into sequence. Bring up to volume with polished D-I H2O.
= Dissolve 3.000 g of Boric Acid; 10.000 g of Manganous Sulfate Monohydrate; 0.250 g of Sodium Molybdate Dihydrate; and 0.750 g of Potassium Iodide in 950.000 ml of polished D-I H2O in sequence. Bring up to volume with polished D-I H2O.
= Dissolve 3.700 g of Disodium EDTA Dihydrate and 2.790 g of Ferrous Sulfate 7-Hydrate into 950.000 ml of D-I H2O. Bring up to volume with D-I H2O.
Total Volume (L) = 1.00

| Ingredient | Amount | Unit |
| --- | --- | --- |
| D-I H2O | 950.000 | ml |
| MS Salts (GIBCO #11117-074) | 4.300 | g |
| Myo-Inositol | 0.100 | g |
| MS Vitamins Stock Solution ## | 5.000 | ml |
| Sucrose | 40.000 | g |
| Bacto-Agar @ | 6.000 | g |

Directions:
@ = Add after bringing up to volume
Dissolve ingredients in polished D-I H2O in sequence
Adjust to pH 5.6
Bring up to volume with polished D-I H2O after adjusting pH
Sterilize and cool to 60° C.
## = Dissolve 0.100 g of Nicotinic Acid; 0.020 g of Thiamine.HCL; 0.100 g of Pyridoxine.HCL; and 0.400 g of Glycine in 875.000 ml of polished D-I H2O in sequence. Bring up to volume with polished D-I H2O. Make in 400 ml portions. Thiamine.HCL & Pyridoxine.HCL are in Dark Desciator. Store for one month, unless contamination or precipitation occur, then make fresh stock.
Total Volume (L) = 1.00

| Ingredient | Amount | Unit |
| --- | --- | --- |
| D-I H2O | 950.000 | ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |

| Ingredient | Amount | Unit |
| --- | --- | --- |
| Indole Acetic Acid 0.5 mg/ml # | 2.000 | ml |
| .1 mM Absissic Acid | 1.000 | ml |
| Bialaphos 1 mg/ml # | 3.000 | ml |

Directions:
@ = Add after bringing up to volume
= Add after sterilizing and cooling to temp.
Dissolve ingredients in polished D-I H2O in sequence
Adjust to pH 5.6
Bring up to volume with polished D-I H2O after adjusting pH
Sterilize and cool to 60° C.
Add 3.5 g/L of Gelrite for Cell Biology
## = Dissolve 0.100 g of Nicotinic Acid; 0.020 g of Thiamine.HCL; 0.100 g of Pyridoxine.HCL; and 0.400 g of Glycine in 875.000 ml of polished D-I H2O in sequence. Bring up to volume with polished D-I H2O. Make in 400 ml portions. Thiamine.HCL & Pyridoxine.HCL are in Dark Desciator. Store for one month, unless contamination or precipitation occur, then make fresh stock.
Total Volume (L) = 1.00

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511) | 0.400 | ml |
| Thiamine .HCL 0.4 mg/ml | 1.250 | ml |
| Sucrose | 20.000 | g |
| 2, 4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@ = Add after bringing up to volume
= Add after sterilizing and cooling to temp.
Dissolve ingredients in D-I H2O in sequence
Adjust to pH 5.8 w/KOH
Bring up to volume with D-I H2O
Sterilize and cool to room temp.
Total Volume (L) = 1.00

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine .HCL 0.4 mg/ml | 1.250 | ml |
| Sucrose | 30.000 | g |
| 2, 4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:
@ = Add after bringing up to volume
= Add after sterilizing and cooling to temp.
Dissolve ingredients in D-I H2O in sequence
Adjust to pH 5.8 w/KOH
Bring up to volume with D-I H2O
Sterilize and cool to room temp.
Total Volume (L) = 1.00

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine .HCL 0.4 mg/ml | 1.250 | ml |
| Sucrose | 120.000 | g |
| 2, 4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@ = Add after bringing up to volume
= Add after sterilizing and cooling to temp.
Dissolve ingredients in D-I H2O in sequence
Adjust to pH 5.8 w/KOH
Bring up to volume with D-I H2O
Sterilize and cool to room temp.
Autoclave less time because of increased sucrose
Total Volume (L) = 1.00

What is claimed is:

1. A method of degrading fumonisin, or a structurally related mycotoxin in a plant, the method comprising the steps of:

a) introducing into plant cells or tissues at least one copy of an expression cassette comprising a polynucleotide from *Exophiala spinifera, Rhinocladiella atrovirens*, or the bacterium deposited as ATCC 55552, said polynucleotide encoding a fumonisin esterase, operably linked to a promoter; and b) expressing fumonisin esterase for a time sufficient to degrade fumonisin or a structurally related mycotoxin.

2. The method of claim 1 wherein the plant or plant cell is a monocot.

3. The method of claim 2 wherein the monocot is selected from the group consisting of maize, sorghum, and rice.

4. The method of claim 1 wherein the plant or plant cell is a dicot.

5. The method of claim 1 wherein the polynucleotide encoding the fumonisin esterase comprises the polynucleotide set forth in SEQ ID NO: 11.

6. The method of claim 1 wherein the polynucleotide encoding the fumonisin esterase comprises the polynucleotide set forth in SEQ ID NO: 15.

7. The method of claim 1 wherein the polynucleotide encoding the fumonisin esterase comprises a polynucleotide having at least 75% identity to the polynucleotide set forth in SEQ ID NO: 11.

8. The method of claim 1 wherein the polynucleotide encoding the fumonisin esterase comprises a polynucleotide having at least 75% identity to the polynucleotide set forth in SEQ ID NO: 15.

9. The method of claim 1 wherein the polynucleotide encoding the fumonisin esterase comprises a polynucleotide capable of hybridizing under highly stringent conditions to SEQ ID NO: 11.

10. The method of claim 1 wherein the polynueleotide encoding the fumonisin esterase comprises a polynucleotide capable of hybridizing under highly stringent conditions to SEQ ID NO: 15.

* * * * *

```
                         SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GGGGAATTCG ARGAYTGNYT NTAYNTNAAY RT                                      32

(2) INFORMATION FOR SEQ ID NO:2:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGGGAATTCM CNGTNNTNVT NTGGATNYAY GGNGGNG                                 37

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGGAAGCTTG GRTYNCCNCC RAANKBNGCD ATRTT                                   35

(2) INFORMATION FOR SEQ ID NO:4:

(i) SEQUENCE CHARACTERISTICS:
        (A) LENGTH: 36 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGGAAGCTTC NCCNGCNSWY TCNCCRAANA DNGTNA                                  36

(2) INFORMATION FOR SEQ ID NO:5:

(i) SEQUENCE CHARACTERISTICS:
        (A) LENGTH: 76 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Ser Phe His Leu Tyr Asp Gly Ala Ser Phe Ala Ala Asn Gln Asp Val
1               5                   10                  15

Ile Val Val Thr Ile Asn Tyr Arg Thr Asn Ile Leu Gly Phe Pro Ala
            20                  25                  30

Ala Pro Gln Leu Pro Ile Thr Gln Arg Asn Leu Gly Phe Leu Asp Gln
        35                  40                  45

Arg Phe Ala Leu Asp Trp Val Gln Arg Asn Ile Ala Ala Phe Gly Gly
    50                  55                  60

Asp Pro Arg Lys Val Thr Phe Phe Gly Glu Ser Ala
65                  70                  75

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCTAGTTTCG CAGCCAATCA GGA                                                23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAAGGCTGCG ATGTTCCGCT GTA                                                23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:
```

```
TCGCTGTGTT ATTGGCAGCT GAG                                                    23
```

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CGCGGATCCG TTTTTTTTTT TTTTTTTV                                               28
```

(2) INFORMATION FOR SEQ ID NO:10:

(i) SEQUENCE CHARACTERISTICS:
        (A) LENGTH: 527 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Met Pro Ser Arg Tyr Ile Leu Ser Trp Leu Leu Thr Cys Phe Leu Gly
1               5                   10                  15

Ile Ala Phe Gly Ser Arg Cys Gly Ser Ser Ala Pro Thr Val Lys Ile
            20                  25                  30

Asp Ala Gly Met Val Val Gly Thr Thr Thr Thr Val Pro Gly Thr Thr
        35                  40                  45

Ala Thr Val Ser Glu Phe Leu Gly Val Pro Phe Ala Ala Ser Pro Thr
    50                  55                  60

Arg Phe Ala Pro Pro Thr Arg Pro Val Pro Trp Ser Thr Pro Leu Gln
65                  70                  75                  80

Ala Thr Ala Tyr Gly Pro Ala Cys Pro Gln Gln Phe Asn Tyr Pro Glu
                85                  90                  95

Glu Leu Arg Glu Ile Thr Met Ala Trp Phe Asn Thr Pro Pro Pro Ser
            100                 105                 110

Ala Gly Glu Ser Glu Asp Cys Leu Asn Leu Asn Ile Tyr Val Pro Gly
        115                 120                 125

Thr Glu Asn Thr Asn Lys Ala Val Met Val Trp Ile Tyr Gly Gly Ala
    130                 135                 140

Leu Glu Tyr Gly Trp Asn Ser Phe His Leu Tyr Asp Gly Ala Ser Phe
145                 150                 155                 160

Ala Ala Asn Gln Asp Val Ile Val Thr Ile Asn Tyr Arg Thr Asn
                165                 170                 175

Ile Leu Gly Phe Pro Ala Ala Pro Gln Leu Pro Ile Thr Gln Arg Asn
            180                 185                 190

Leu Gly Phe Leu Asp Gln Arg Phe Ala Leu Asp Trp Val Gln Arg Asn
        195                 200                 205

Ile Ala Ala Phe Gly Gly Asp Pro Arg Lys Val Thr Ile Phe Gly Gln
    210                 215                 220

Ser Ala Gly Gly Arg Ser Val Asp Val Leu Leu Thr Ser Met Pro His
225                 230                 235                 240

Asn Pro Pro Phe Arg Ala Ala Ile Met Glu Ser Gly Val Ala Asn Tyr
                245                 250                 255
```

-continued

```
Asn Phe Pro Lys Gly Asp Leu Ser Glu Pro Trp Asn Thr Thr Val Gln
            260                 265                 270

Ala Leu Asn Cys Thr Thr Ser Ile Asp Ile Leu Ser Cys Met Arg Arg
            275                 280                 285

Val Asp Leu Ala Thr Leu Met Asn Thr Ile Glu Gln Leu Gly Leu Gly
            290                 295                 300

Phe Glu Tyr Thr Leu Asp Asn Val Thr Val Tyr Arg Ser Glu Thr
305                 310                 315                 320

Ala Arg Thr Thr Gly Asp Ile Ala Arg Val Pro Val Leu Val Gly Thr
                325                 330                 335

Val Ala Asn Asp Gly Leu Leu Phe Val Leu Gly Glu Asn Asp Thr Gln
            340                 345                 350

Ala Tyr Leu Glu Glu Ala Ile Pro Asn Gln Pro Asp Leu Tyr Gln Thr
            355                 360                 365

Leu Leu Gly Ala Tyr Pro Ile Gly Ser Pro Gly Ile Gly Ser Pro Gln
        370                 375                 380

Asp Gln Ile Ala Ala Ile Glu Thr Glu Val Arg Phe Gln Cys Pro Ser
385                 390                 395                 400

Ala Ile Val Ala Gln Asp Ser Arg Asn Arg Gly Ile Pro Ser Trp Arg
                405                 410                 415

Tyr Tyr Tyr Asn Ala Thr Phe Glu Asn Leu Glu Leu Phe Pro Gly Ser
            420                 425                 430

Glu Val Tyr His Ser Ser Glu Val Gly Met Val Phe Gly Thr Tyr Pro
            435                 440                 445

Val Ala Ser Ala Thr Ala Leu Glu Ala Gln Thr Ser Lys Tyr Met Gln
        450                 455                 460

Gly Ala Trp Ala Ala Phe Ala Lys Asn Pro Met Asn Gly Pro Gly Trp
465                 470                 475                 480

Lys Gln Val Pro Asn Val Ala Ala Leu Gly Ser Pro Gly Lys Ala Ile
                485                 490                 495

Gln Val Asp Val Ser Pro Ala Thr Ile Asp Gln Arg Cys Ala Leu Tyr
            500                 505                 510

Thr His Tyr Tyr Thr Glu Leu Gly Thr Ile Ala Pro Arg Thr Phe
        515                 520                 525
```

(2) INFORMATION FOR SEQ ID NO:11:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
ACTAGTGGAT CATTGCATTG GCTGGCGGAC TGGCGCGCCG ATAGTCGTTG CGATGGTCGC     60

GAGAATAAGC GTGCGAAGTG GGAGGATGTG AAGATGGGGG CCAGGAGTAT GTGTGCGGGA    120

CGGTTCGGAC GCTTCTGCAT TGGCTTGGCT TCATCGGTTG CCGTGACTCT AGGGGGAGCC    180

TCCGCCGCCG GCGCGGCAAC CGCGACGGAT TTTCCGGTCC GCAGGACCGA TCTGGGCCAG    240

GTTCAGGGAC TGGCCGGGGA CGTGATGAGC TTTCGCGGAA TACCCTATGC AGCGCCGCCG    300

GTGGGCGGGC TGCGTTGGAA GCCGCCCCAA CACGCCCGGC CCTGGGCGGG CGTTCGCCCC    360

GCCACCCAAT TTGGCTCCGA CTGCTTCGGC GCGGCCTATC TTCGCAAAGG CAGCCTCGCC    420

CCCGGCGTGA GCGAGGACTG TCTTTACCTC AACGTATGGG CGCCGTCAGG CGCTAAACCC    480
```

-continued

```
GGCCAGTACC CCGTCATGGT CTGGGTCTAC GGCGGCGGCT TCGCCGGCGG CACGGCCGCC    540

ATGCCCTACT ACGACGGCGA GGCGCTTGCG CGACAGGGCG TCGTCGTGGT GACGTTTAAC    600

TATCGGACGA ACATCCTGGG CTTTTTCGCC CATCCTGGTC TCTCGCGCGA GAGCCCCACC    660

GGAACTTCGG GCAACTACGG CCTACTCGAC ATTCTCGCCG CTCTTCGGTG GGTGCAGAGC    720

AACGCCCGCG CCTTCGGAGG GGACCCCGGC CGAGTGACGG TCTTTGGTGA ATCGGCCGGA    780

GCGAGCGCGA TCGGACTTCT GCTCACCTCG CCGCTGAGCA AGGGTCTCTT CCGTGGCGCT    840

ATCCTCGAAA GTCCAGGGCT GACGCGACCG CTCGCGACGC TCGCCGACAG CGCCGCCTCG    900

GGCGAGCGCC TCGACGCCGA TCTTTCGCGA CTGCGCTCGA CCGACCCAGC CACCCTGATG    960

GCGCGCGCCG ACGCGGCCCG CCCGGCATCG CGGGACCTGC GCAGGCCGCG TCCGACCGGA   1020

CCGATCGTCG ATGGCCATGT GCTGCCGCAG ACCGACAGCG CGGCGATCGC GGCGGGGCAG   1080

CTGGCGCCGG TTCGGGTCCT GATCGGAACC AATGCCGACG AAGGCCGCGC CTTCCTCGGG   1140

CGCGCGCCGA TGGAGACGCC AGCGGACTAC CAAGCCTATC TGGAGGCGCA GTTTGGCGAC   1200

CAAGCCGCCG CCGTGGCGGC GTGCTATCCC CTCGACGGCC GGGCCACGCC CAAGGAAATG   1260

GTCGCGCGCA TCTTCGGCGA CAATCAGTTC AATCGGGGGG TCTCGGCCTT CTCGGAAGCG   1320

CTTGTGCGCC AGGGCGCGCC CGTGTGGCGT TATCAGTTCA ACGGTAATAC CGAGGGTGGA   1380

AGAGCGCCGG CTACCCACGG AGCCGAAATT CCCTACGTTT TCGGGGTGTT CAAGCTCGAC   1440

GAGTTGGGTC TGTTCGATTG GCCGCCCGAG GGGCCCACGC CCGCCGACCG TGCGCTGGGC   1500

CAACTGATGT CCTCCGCCTG GGTCCGGTTC GCCAAGAATG GCGACCCCGC CGGGGACGCC   1560

CTTACCTGGC CTGCCTATTC TACGGGCAAG TCGACCATGA CATTCGGTCC CGAGGGCCGC   1620

GCGGCGGTGG TGTCGCCCGG ACCTTCCATC CCCCCTTGCG CGGATGGCGC CAAGGCGGGG   1680

TGACGCCGTC GACGATGGCG TGACGACGGT CGAGGCGATG TTCTCGATCT GGAGTCCGCG   1740

CCGCCTCGAT TTGCGTCGTC TCCGGCGCTC AGACGAACGC CCCAGTTCCA TCCACACAGT   1800
```

(2) INFORMATION FOR SEQ ID NO:12:

(i) SEQUENCE CHARACTERISTICS:
        (A) LENGTH: 529 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Met Gly Ala Arg Ser Met Cys Ala Gly Arg Phe Gly Arg Phe Cys Ile
 1               5                  10                  15

Gly Leu Ala Ser Ser Val Ala Val Thr Leu Gly Gly Ala Ser Ala Ala
            20                  25                  30

Gly Ala Ala Thr Ala Thr Asp Phe Pro Val Arg Arg Thr Asp Leu Gly
        35                  40                  45

Gln Val Gln Gly Leu Ala Gly Asp Val Met Ser Phe Arg Gly Ile Pro
    50                  55                  60

Tyr Ala Ala Pro Pro Val Gly Leu Arg Trp Lys Pro Pro Gln His
65                  70                  75                  80

Ala Arg Pro Trp Ala Gly Val Arg Pro Ala Thr Gln Phe Gly Ser Asp
                85                  90                  95

Cys Phe Gly Ala Ala Tyr Leu Arg Lys Gly Ser Leu Ala Pro Gly Val
            100                 105                 110
```

-continued

```
Ser Glu Asp Cys Leu Tyr Leu Asn Val Trp Ala Pro Ser Gly Ala Lys
        115                 120                 125

Pro Gly Gln Tyr Pro Val Met Val Trp Val Tyr Gly Gly Phe Ala
130                 135                 140

Gly Gly Thr Ala Ala Met Pro Tyr Tyr Asp Gly Glu Ala Leu Ala Arg
145                 150                 155                 160

Gln Gly Val Val Val Thr Phe Asn Tyr Arg Thr Asn Ile Leu Gly
                165                 170                 175

Phe Phe Ala His Pro Gly Leu Ser Arg Glu Ser Pro Thr Gly Thr Ser
            180                 185                 190

Gly Asn Tyr Gly Leu Leu Asp Ile Leu Ala Ala Leu Arg Trp Val Gln
        195                 200                 205

Ser Asn Ala Arg Ala Phe Gly Gly Asp Pro Gly Arg Val Thr Val Phe
210                 215                 220

Gly Glu Ser Ala Gly Ala Ser Ala Ile Gly Leu Leu Leu Thr Ser Pro
225                 230                 235                 240

Leu Ser Lys Gly Leu Phe Arg Gly Ala Ile Leu Glu Ser Pro Gly Leu
                245                 250                 255

Thr Arg Pro Leu Ala Thr Leu Ala Asp Ser Ala Ala Ser Gly Glu Arg
            260                 265                 270

Leu Asp Ala Asp Leu Ser Arg Leu Arg Ser Thr Asp Pro Ala Thr Leu
        275                 280                 285

Met Ala Arg Ala Asp Ala Ala Arg Pro Ala Ser Arg Asp Leu Arg Arg
290                 295                 300

Pro Arg Pro Thr Gly Pro Ile Val Asp Gly His Val Leu Pro Gln Thr
305                 310                 315                 320

Asp Ser Ala Ala Ile Ala Ala Gly Gln Leu Ala Pro Val Arg Val Leu
                325                 330                 335

Ile Gly Thr Asn Ala Asp Glu Gly Arg Ala Phe Leu Gly Arg Ala Pro
            340                 345                 350

Met Glu Thr Pro Ala Asp Tyr Gln Ala Tyr Leu Glu Ala Gln Phe Gly
        355                 360                 365

Asp Gln Ala Ala Ala Val Ala Ala Cys Tyr Pro Leu Asp Gly Arg Ala
370                 375                 380

Thr Pro Lys Glu Met Val Ala Arg Ile Phe Gly Asp Asn Gln Phe Asn
385                 390                 395                 400

Arg Gly Val Ser Ala Phe Ser Glu Ala Leu Val Arg Gln Gly Ala Pro
                405                 410                 415

Val Trp Arg Tyr Gln Phe Asn Gly Asn Thr Glu Gly Gly Arg Ala Pro
            420                 425                 430

Ala Thr His Gly Ala Glu Ile Pro Tyr Val Phe Gly Val Phe Lys Leu
        435                 440                 445

Asp Glu Leu Gly Leu Phe Asp Trp Pro Pro Glu Gly Pro Thr Pro Ala
450                 455                 460

Asp Arg Ala Leu Gly Gln Leu Met Ser Ser Ala Trp Val Arg Phe Ala
465                 470                 475                 480

Lys Asn Gly Asp Pro Ala Gly Asp Ala Leu Thr Trp Pro Ala Tyr Ser
                485                 490                 495

Thr Gly Lys Ser Thr Met Thr Phe Gly Pro Glu Gly Arg Ala Ala Val
            500                 505                 510

Val Ser Pro Gly Pro Ser Ile Pro Pro Cys Ala Asp Gly Ala Lys Ala
        515                 520                 525

Gly
```

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CATATGGCTA GCGCTCCTAC TGTCAAGATT GATGCT                                 36
```

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GACGAGCTCC GCTGTAGGTA CAATACCCGG GTCCT                                  35
```

(2) INFORMATION FOR SEQ ID NO:15:

(i) SEQUENCE CHARACTERISTICS:
        (A) LENGTH: 1937 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
GCGGATCCGT TTTTTTTTTT TTTTTTCCTA AGTTCGACTA CCCACTTGCT AGTCTCACAG        60
TAGCTCCAAG GGTATAAGTT CGACTCGAAG CTGCATCTCT CCGTGAAACA TGGCAATAGT       120
TTTTGTAGAC AGATCCATCA ACCGAGTACA CGATGCCGTC AAGGTACATT CTCTCTTGGC       180
TCCTCACCTG CTTTTTGGGC ATTGCTTTTG GCTCACGATG CGGGTCGTCT GCTCCTACTG       240
TCAAGATTGA TGCTGGGATG GTGGTCGGCA CGACTACTAC TGTCCCCGGC ACCACTGCGA       300
CCGTCAGCGA GTTCTTGGGC GTTCCTTTTG CCGCCTCTCC GACACGATTT GCGCCTCCTA       360
CTCGTCCCGT GCCTTGGTCA ACGCCTTTGC AAGCCACTGC ATATGGTCCA GCATGCCCTC       420
AACAATTCAA TTACCCCGAA GAACTCCGTG AGATTACGAT GGCCTGGTTC AATACACCGC       480
CCCCGTCAGC TGGTGAAAGT GAGGACTGCC TGAACCTCAA CATCTACGTC CCAGGAACTG       540
AGAACACAAA CAAAGCCGTC ATGGTTTGGA TATACGGTGG AGCGCTGGAA TATGGTTGGA       600
ATTCATTCCA CCTTTACGAC GGGGCTAGTT TCGCAGCCAA TCAGGATGTC ATCGTCGTGA       660
CCATCAACTA CAGAACGAAC ATTCTGGGGT TCCCTGCTGC CCCTCAGCTT CCAATAACAC       720
AGCGAAATCT GGGGTTCCTA GACCAAAGGT TTGCTTTGGA TTGGGTACAG CGGAACATCG       780
CAGCCTTTGG CGGTGATCCT CGAAAGGTCA ATATATTTGG GCAGAGTGCG GGGGCAGAA        840
GTGTCGACGT CCTCTTGACG TCTATGCCAC ACAACCCACC CTTCCGAGCA GCAATCATGG       900
AGTCCGGTGT GGCTAACTAC AACTTCCCCA AGGGAGATTT GTCCGAACCT TGGAACACCA       960
CTGTTCAAGC TCTCAACTGT ACCACCAGTA TCGACATCTT GAGTTGTATG AGAAGAGTCG      1020
ATCTCGCCAC TCTGATGAAC ACGATCGAGC AACTCGGACT TGGGTTTGAG TACACGTTGG      1080
```

-continued

```
ACAACGTAAC GGTTGTGTAC CGTTCTGAAA CGGCTCGCAC GACTGGTGAC ATTGCTCGTG    1140

TACCTGTTCT CGTCGGGACG GTGGCCAACG ACGGACTTCT CTTTGTCCTC GGGGAGAATG    1200

ACACCCAAGC ATATCTCGAG GAGGCAATCC CGAATCAGCC CGACCTTTAC CAGACTCTCC    1260

TTGGAGCATA TCCCATTGGA TCCCCAGGGA TCGGATCGCC TCAAGATCAG ATTGCCGCCA    1320

TTGAGACCGA GGTAAGATTC CAGTGTCCTT CTGCCATCGT GGCTCAGGAC TCCCGGAATC    1380

GGGGTATCCC TTCTTGGCGC TACTACTACA ATGCGACCTT TGAGAATCTG GAGCTTTTCC    1440

CTGGGTCCGA AGTGTACCAC AGCTCTGAAG TCGGATGGT GTTTGGCACG TATCCTGTCG     1500

CAAGTGCGAC CGCCTTGGAG GCCCAGACGA GCAAATACAT GCAGGGTGCC TGGGCGGCCT    1560

TTGCCAAAAA CCCCATGAAT GGGCCTGGGT GGAAACAAGT GCCGAATGTC GCGGCGCTTG    1620

GCTCACCAGG CAAAGCCATC CAGGTTGACG TCTCTCCAGC GACAATAGAC CAACGATGTG    1680

CCTTGTACAC GCATTATTAT ACTGAGTTGG GCACAATCGC GCCGAGGACA TTTTGAGGAC    1740

CAGGGTATTG TACCTACAGC GGGTTCGGAA AAGGAGGTAT CTGCTGTCAA TTTGCCGCCA    1800

GCCATCATTG AAGAGTGCTG AAATTTCATG GGGGAATATC CATCCATGCT CACATTAGCG    1860

CTTTTGGAAG ATGGACTGTT AGCGAGTCTT GGGCGGTTTC AGGCTTTTCC CCCCCCAAAA    1920

AAAAAAAAAA AAAAAA                                                    1937
```

(2) INFORMATION FOR SEQ ID NO:16:

(i) SEQUENCE CHARACTERISTICS:
    (A) LENGTH: 525 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:16:

```
Met Ala Asn Lys His Leu Ser Leu Ser Leu Phe Leu Val Leu Leu Gly
 1               5                  10                  15

Leu Ser Ala Ser Leu Ala Ser Gly Ala Pro Thr Val Lys Ile Asp Ala
             20                  25                  30

Gly Met Val Val Gly Thr Thr Thr Thr Val Pro Gly Thr Thr Ala Thr
         35                  40                  45

Val Ser Glu Phe Leu Gly Val Pro Phe Ala Ala Ser Pro Thr Arg Phe
     50                  55                  60

Ala Pro Pro Thr Arg Pro Val Pro Trp Ser Thr Pro Leu Gln Ala Thr
65                  70                  75                  80

Ala Tyr Gly Pro Ala Cys Pro Gln Gln Phe Asn Tyr Pro Glu Glu Leu
                 85                  90                  95

Arg Glu Ile Thr Met Ala Trp Phe Asn Thr Pro Pro Ser Ala Gly
            100                 105                 110

Glu Ser Glu Asp Cys Leu Asn Leu Asn Ile Tyr Val Pro Gly Thr Glu
        115                 120                 125

Asn Thr Asn Lys Ala Val Met Val Trp Ile Tyr Gly Gly Ala Leu Glu
    130                 135                 140

Tyr Gly Trp Asn Ser Phe His Leu Tyr Asp Gly Ala Ser Phe Ala Ala
145                 150                 155                 160

Asn Gln Asp Val Ile Val Val Thr Ile Asn Tyr Arg Thr Asn Ile Leu
                165                 170                 175

Gly Phe Pro Ala Ala Pro Gln Leu Pro Ile Thr Gln Arg Asn Leu Gly
            180                 185                 190
```

-continued

```
Phe Leu Asp Gln Arg Phe Ala Leu Asp Trp Val Gln Arg Asn Ile Ala
            195                 200                 205
Ala Phe Gly Gly Asp Pro Arg Lys Val Thr Ile Phe Gly Gln Ser Ala
        210                 215                 220
Gly Gly Arg Ser Val Asp Val Leu Leu Thr Ser Met Pro His Asn Pro
225                 230                 235                 240
Pro Phe Arg Ala Ala Ile Met Glu Ser Gly Val Ala Asn Tyr Asn Phe
                245                 250                 255
Pro Lys Gly Asp Leu Ser Glu Pro Trp Asn Thr Thr Val Gln Ala Leu
            260                 265                 270
Asn Cys Thr Thr Ser Ile Asp Ile Leu Ser Cys Met Arg Arg Val Asp
        275                 280                 285
Leu Ala Thr Leu Met Asn Thr Ile Glu Gln Leu Gly Leu Gly Phe Glu
    290                 295                 300
Tyr Thr Leu Asp Asn Val Thr Val Val Tyr Arg Ser Glu Thr Ala Arg
305                 310                 315                 320
Thr Thr Gly Asp Ile Ala Arg Val Pro Val Leu Val Gly Thr Val Ala
                325                 330                 335
Asn Asp Gly Leu Leu Phe Val Leu Gly Glu Asn Asp Thr Gln Ala Tyr
            340                 345                 350
Leu Glu Glu Ala Ile Pro Asn Gln Pro Asp Leu Tyr Gln Thr Leu Leu
        355                 360                 365
Gly Ala Tyr Pro Ile Gly Ser Pro Gly Ile Gly Ser Pro Gln Asp Gln
    370                 375                 380
Ile Ala Ala Ile Glu Thr Glu Val Arg Phe Gln Cys Pro Ser Ala Ile
385                 390                 395                 400
Val Ala Gln Asp Ser Arg Asn Arg Gly Ile Pro Ser Trp Arg Tyr Tyr
                405                 410                 415
Tyr Asn Ala Thr Phe Glu Asn Leu Glu Leu Phe Pro Gly Ser Glu Val
            420                 425                 430
Tyr His Ser Ser Glu Val Gly Met Val Phe Gly Thr Tyr Pro Val Ala
        435                 440                 445
Ser Ala Thr Ala Leu Glu Ala Gln Thr Ser Lys Tyr Met Gln Gly Ala
    450                 455                 460
Trp Ala Ala Phe Ala Lys Asn Pro Met Asn Gly Pro Gly Trp Lys Gln
465                 470                 475                 480
Val Pro Asn Val Ala Ala Leu Gly Ser Pro Gly Lys Ala Ile Gln Val
                485                 490                 495
Asp Val Ser Pro Ala Thr Ile Asp Gln Arg Cys Ala Leu Tyr Thr His
            500                 505                 510
Tyr Tyr Thr Glu Leu Gly Thr Ile Ala Pro Arg Thr Phe
        515                 520                 525
```

(2) INFORMATION FOR SEQ ID NO:17:

(i) SEQUENCE CHARACTERISTICS:
        (A) LENGTH: 516 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

```
Met Ala Asn Lys His Leu Ser Leu Ser Leu Phe Leu Val Leu Leu Gly
1               5                   10                  15
```

-continued

```
Leu Ser Ala Ser Leu Ala Ser Gly Thr Asp Phe Pro Val Arg Arg Thr
            20                  25                  30

Asp Leu Gly Gln Val Gln Gly Leu Ala Gly Asp Val Met Ser Phe Arg
            35                  40                  45

Gly Ile Pro Tyr Ala Ala Pro Pro Val Gly Leu Arg Trp Lys Pro
50                      55                  60

Pro Gln His Ala Arg Pro Trp Ala Gly Val Arg Pro Ala Thr Gln Phe
65                      70                  75                  80

Gly Ser Asp Cys Phe Gly Ala Ala Tyr Leu Arg Lys Gly Ser Leu Ala
                85                  90                  95

Pro Gly Val Ser Glu Asp Cys Leu Tyr Leu Asn Val Trp Ala Pro Ser
            100                 105                 110

Gly Ala Lys Pro Gly Gln Tyr Pro Val Met Val Trp Val Tyr Gly Gly
            115                 120                 125

Gly Phe Ala Gly Gly Thr Ala Ala Met Pro Tyr Tyr Asp Gly Glu Ala
            130                 135                 140

Leu Ala Arg Gln Gly Val Val Val Thr Phe Asn Tyr Arg Thr Asn
145                 150                 155                 160

Ile Leu Gly Phe Phe Ala His Pro Gly Leu Ser Arg Glu Ser Pro Thr
                165                 170                 175

Gly Thr Ser Gly Asn Tyr Gly Leu Leu Asp Ile Leu Ala Ala Leu Arg
                180                 185                 190

Trp Val Gln Ser Asn Ala Arg Ala Phe Gly Gly Asp Pro Gly Arg Val
            195                 200                 205

Thr Val Phe Gly Glu Ser Ala Gly Ala Ser Ala Ile Gly Leu Leu Leu
            210                 215                 220

Thr Ser Pro Leu Ser Lys Gly Leu Phe Arg Gly Ala Ile Leu Glu Ser
225                 230                 235                 240

Pro Gly Leu Thr Arg Pro Leu Ala Thr Leu Ala Asp Ser Ala Ala Ser
                245                 250                 255

Gly Glu Arg Leu Asp Ala Asp Leu Ser Arg Leu Arg Ser Thr Asp Pro
            260                 265                 270

Ala Thr Leu Met Ala Arg Ala Asp Ala Ala Arg Pro Ala Ser Arg Asp
            275                 280                 285

Leu Arg Arg Pro Arg Pro Thr Gly Pro Ile Val Asp Gly His Val Leu
            290                 295                 300

Pro Gln Thr Asp Ser Ala Ala Ile Ala Ala Gly Gln Leu Ala Pro Val
305                 310                 315                 320

Arg Val Leu Ile Gly Thr Asn Ala Asp Glu Gly Arg Ala Phe Leu Gly
                325                 330                 335

Arg Ala Pro Met Glu Thr Pro Ala Asp Tyr Gln Ala Tyr Leu Glu Ala
                340                 345                 350

Gln Phe Gly Asp Gln Ala Ala Ala Val Ala Ala Cys Tyr Pro Leu Asp
            355                 360                 365

Gly Arg Ala Thr Pro Lys Glu Met Val Ala Arg Ile Phe Gly Asp Asn
            370                 375                 380

Gln Phe Asn Arg Gly Val Ser Ala Phe Ser Glu Ala Leu Val Arg Gln
385                 390                 395                 400

Gly Ala Pro Val Trp Arg Tyr Gln Phe Asn Gly Asn Thr Glu Gly Gly
                405                 410                 415

Arg Ala Pro Ala Thr His Gly Ala Glu Ile Pro Tyr Val Phe Gly Val
            420                 425                 430
```

-continued

| | | | | | | | | | | | | | | | |
|---|---|---|---|---|---|---|---|---|---|---|---|---|---|---|---|
| Phe | Lys | Leu | Asp | Glu | Leu | Gly | Leu | Phe | Asp | Trp | Pro | Pro | Glu | Gly | Pro |
| | | 435 | | | | | 440 | | | | | 445 | | | |
| Thr | Pro | Ala | Asp | Arg | Ala | Leu | Gly | Gln | Leu | Met | Ser | Ser | Ala | Trp | Val |
| | 450 | | | | | 455 | | | | | 460 | | | | |
| Arg | Phe | Ala | Lys | Asn | Gly | Asp | Pro | Ala | Gly | Asp | Ala | Leu | Thr | Trp | Pro |
| 465 | | | | | 470 | | | | | 475 | | | | | 480 |
| Ala | Tyr | Ser | Thr | Gly | Lys | Ser | Thr | Met | Thr | Phe | Gly | Pro | Glu | Gly | Arg |
| | | | | 485 | | | | | 490 | | | | | 495 | |
| Ala | Ala | Val | Val | Ser | Pro | Gly | Pro | Ser | Ile | Pro | Pro | Cys | Ala | Asp | Gly |
| | | | 500 | | | | | 505 | | | | | 510 | | |
| Ala | Lys | Ala | Gly | | | | | | | | | | | | |
| | | 515 | | | | | | | | | | | | | |